US007716072B1

(12) United States Patent
Green, Jr. et al.

(10) Patent No.: US 7,716,072 B1
(45) Date of Patent: May 11, 2010

(54) INTEGRATED MEDICAL SOFTWARE SYSTEM

(75) Inventors: W. Thomas Green, Jr., Carrollton, GA (US); W. Thomas Green, III, Carrollton, GA (US); Deborah I. Esslinger, Carrollton, GA (US); Robert D. Taylor, Douglasville, GA (US); Susan Burson Tice, Carrollton, GA (US); Elizabeth W. Turner, Carrollton, GA (US); Gregory H. Schulenburg, Carrollton, GA (US)

(73) Assignee: Greenway Medical Technologies, Inc., Carrollton, GA (US)

( * ) Notice: Subject to any disclaimer, the term of this patent is extended or adjusted under 35 U.S.C. 154(b) by 62 days.

(21) Appl. No.: 11/730,078

(22) Filed: Mar. 29, 2007

Related U.S. Application Data

(62) Division of application No. 10/202,627, filed on Jul. 25, 2002.

(60) Provisional application No. 60/373,662, filed on Apr. 19, 2002.

(51) Int. Cl.
*A61B 5/00* (2006.01)
*G06F 19/00* (2006.01)

(52) U.S. Cl. ........................................................ 705/3

(58) Field of Classification Search ........................ None
See application file for complete search history.

(56) References Cited

U.S. PATENT DOCUMENTS

| | | | |
|---|---|---|---|
| 3,597,742 A | 8/1971 | Philipps et al. | |
| 5,065,315 A | 11/1991 | Garcia | |
| 5,359,509 A | 10/1994 | Little et al. | |

(Continued)

FOREIGN PATENT DOCUMENTS

WO  WO 95/12857  5/1995

OTHER PUBLICATIONS

Anonymous. Charting eases onto the information highway. Medical Economics. Oradell: Jul. 25, 1994, vol. 71, Issue 14; p. 82.*

(Continued)

*Primary Examiner*—Gerald J. O'Connor
*Assistant Examiner*—Sheetal R Rangrej
(74) *Attorney, Agent, or Firm*—Blank Rome LLP

(57) ABSTRACT

A medical management system is provided that integrates all aspects of healthcare provider practice management and managed care, including schedule management, patient registration, insurance information, EMR and billing and collections. The system integrates a central framework module, a scheduling module, a registration module, an account management module and an electronic record module to provide a seamless exchange of information. A clinical module provides template builder which allows the users to define a customized template. The custom and standard templates are used by a document builder to generate documents, such as progress notes and H&P notes, which are retained in the patient's electronic chart. The progress note template allows the clinician to record a patient encounter by presenting the clinician with predefined sections and sentences that are easily completed by the clinician during or after the patient encounter. The templates and documents generated are designed to closely resemble a paper chart. Information gathered during patient scheduling and triage are referenced to pre-populate the templates to avoid having the clinician entering redundant information. The documents are relied upon to automatically generate patient superbills and electronic requests are sent to a claims clearinghouse.

24 Claims, 38 Drawing Sheets

U.S. PATENT DOCUMENTS

| | | | | |
|---|---|---|---|---|
| 5,361,202 | A | 11/1994 | Doue | |
| 5,572,422 | A | 11/1996 | Nematbakhsh et al. | |
| 5,644,778 | A | 7/1997 | Burks et al. | |
| 5,659,741 | A | 8/1997 | Eberhardt | |
| 5,664,207 | A | 9/1997 | Crumpler et al. | |
| 5,704,044 | A | 12/1997 | Tarter et al. | |
| 5,748,907 | A | 5/1998 | Crane | |
| 5,758,095 | A | 5/1998 | Albaum et al. | |
| 5,772,585 | A * | 6/1998 | Lavin et al. | 600/300 |
| 5,823,948 | A | 10/1998 | Ross, Jr. et al. | |
| 5,826,237 | A | 10/1998 | Macrae et al. | |
| 5,827,180 | A | 10/1998 | Goodman | |
| 5,832,488 | A | 11/1998 | Eberhardt | |
| 5,845,253 | A | 12/1998 | Rensimer et al. | |
| 5,857,967 | A | 1/1999 | Frid et al. | |
| 5,899,998 | A | 5/1999 | McGauley et al. | |
| 5,903,889 | A | 5/1999 | de la Huerga et al. | |
| 5,911,687 | A | 6/1999 | Sato et al. | |
| 5,915,241 | A | 6/1999 | Giannini | |
| 5,924,074 | A | 7/1999 | Evans | |
| 5,933,809 | A | 8/1999 | Hunt et al. | |
| 5,940,802 | A | 8/1999 | Hildebrand et al. | |
| 5,946,659 | A | 8/1999 | Lancelot et al. | |
| 5,950,630 | A | 9/1999 | Portwood et al. | |
| 5,956,690 | A | 9/1999 | Haggerson et al. | |
| 5,991,729 | A | 11/1999 | Barry et al. | |
| 5,991,730 | A | 11/1999 | Lubin et al. | |
| 5,995,937 | A | 11/1999 | DeBusk et al. | |
| 5,995,939 | A | 11/1999 | Berman et al. | |
| 6,004,276 | A | 12/1999 | Wright et al. | |
| 6,018,713 | A | 1/2000 | Coli et al. | |
| 6,024,699 | A | 2/2000 | Surwit et al. | |
| 6,283,761 | B1 | 9/2001 | Joao | |
| 6,289,316 | B1 | 9/2001 | Aghili et al. | |
| 6,314,556 | B1 | 11/2001 | DeBusk et al. | |
| 6,347,329 | B1 | 2/2002 | Evans | |
| 6,374,229 | B1 | 4/2002 | Lowrey et al. | |
| 7,461,079 | B2 | 12/2008 | Walker et al. | |
| 2002/0103811 | A1 * | 8/2002 | Fankhauser et al. | 707/104.1 |

OTHER PUBLICATIONS

Canadian Datasystems. A cure for the paper plague, May 1991, vol. 23, Issue 14; p. D13.*

PR Newswire. Homestead.com helps people jump start their web sites with customizable templates and site building resources, New York: Feb. 7, 2000; p. 1.*

Gilnert, Susan, By design adds tools and clip art. Computer Shopper, Jun. 1994, vol. 14, No. 6, p. 494.*

* cited by examiner

HENT
  ☑⊞ earache
Cardiovascular
  ☑⊞ cardiac murmur in ventrical right
  ☐⊞ mild chest pain in chest wall right midsternal; functional worsens with ambulation
Respiratory
  ☐☐ shortness of breath    ☐☐ deep pain    ☐☐ chronic cough

B C Full Exam
B C Cardiovascular
   Auscultation
   Palpation
   Carotid arteries
   Abdominal aorta.
   Femoral a
   Pedal pulses
   Peripheral circulation

FIG. 33 cal Exam

☐☐Full Exam
  ☐☐Cardiovascular
    Auscultation:          ☐ normal cardiac rate        ☐ normal cardiac rhythm
    Palpation    Rate
    Carotid a    Rhythm                  abnormal S1
                 S1                       loud S1
    Abdominal aorta:                      reduced intensity of S1
    Femoral a.:                           reversed split of S1
    Pedal pulses:                         widened split of first heart sound
    Peripheral circulation:               s>1<

LOCATIONS FOR A SELECTED SYSTEM

FINDINGS MARKED IN RED HAVE BEEN EDITED FROM THEIR DEFAULT VALUE.

CLICK TO ADD VITALS

CLICK TO EDIT MODIFIERS FOR THE FINDING.

FINDINGS IN EDIT MODE.

FINDINGS WITH THEIR DEFAULT VALUES AND MODIFIERS WHICH HAVE BEEN SELECTED FOR THIS SYSTEM ON THE PHYSICAL EXAM PAGE OF THE TEMPLATE BUILDER UPON WHICH THIS NOTE IS BASED.

CLICK ONE OF THESE OPTIONS TO SPECIFY WHICH FINDINGS WILL BE PLACED IN EDIT MODE.

LIST OF SYSTEMS. CLICK A SYSTEM TO PLACE ITS FINDINGS IN EDIT MODE.

T: ONLY SELECTED FINDINGS

C: ALL FINDS IN THE LOCATION

F: ALL FINDINGS FOR ONE OR MORE FOCUSED MACROS

FIG. 40

FINDINGS, MACRO FINDINGS, AND SLECTED FINDINGS ARE BASED ON THE VALUES SET FOR THE PHYSICAL EXAM PORTION OF THE TEMPLATE UPON WHICH THIS NOTE IS BASED.

INTEGRATED MEDICAL SOFTWARE SYSTEM

RELATED APPLICATIONS

The present application is a divisional application of U.S. patent application Ser. No. 10/202,627, filed Jul. 25, 2002, which claims priority to Provisional Application Ser. No. 60/373,662, filed Apr. 19, 2002.

BACKGROUND OF THE INVENTION

Service professionals that regularly schedule patient visits have historically relied upon manual practice management, patient records and managed care (i.e., insurance) techniques. For instance, scheduling patients, tracking prescription orders, and maintaining file documentation are typically performed through paper calendars and files. An office assistant receives and schedules patient appointments on the paper calendar. The service professional then checks the paper schedule for each day.

For purposes of this application, service professionals may include, for instance, healthcare providers such as physicians (MD or DO), dentists, chiropractors, psychologists, and counselors. However, the terms "clinician" or "physician" as used herein are understood to include any service professional or healthcare provider who treats a patient, including for instance physicians, nurses, technicians, therapists, chiropractors, physicians assistant, midwife, psychologists, and counselors.

All information concerning the patient's medical history, such as clinician observations, thoughts, treatments administered, patient history, medication lists, vaccine administration lists, laboratory reports, X-rays, charts, progress notes, consultation reports, hospital reports, correspondence and test results, have traditionally been kept in the paper file. Much of this information is handwritten and signed by the clinician, or transcribed from clinician dictation. Paper-based medical files are typically filed alphabetically by the patient's last name, with the patient's name, date of birth and any known allergies on the outside of the file.

However, manual practice management, patient record and managed care techniques are inefficient since they require a great deal of interaction between the service professional and the office assistant. Last minute scheduling changes often result in lost time for the service professional. In addition, manual tracking is prone to error and the large amounts of paper that is generated take up valuable office space. A small office of 2-3 physicians, for instance, can have approximately 20,000 or more active patients, and therefore anywhere from about 25,000 to 60,000 patient files, depending upon how long they have been in practice.

Since the medical record is paper-based and manually produced, the information needed to bill a patient must be manually entered into the billing application. Clinician orders that often generate billable procedures are difficult to process because they are written by hand and in many cases are omitted from the patient's bill. In addition, handwritten orders for prescriptions have been identified as the number one cause of medical errors resulting in patient death in the United States. Add to these issues the complexity of insurance contracts and procedure fee schedules that govern the amount which clinicians are to be paid for their services, and the result is a very inefficient, labor-intensive process requiring many checks and balances to ensure accurate processing.

In a typical office visit for a medical clinician, the clinician will review his/her schedule for that day or week. In any given day, the clinician may have 20-80 office visits, and up to 2 (or more) medical procedures. Prior to a scheduled examination, the clinician will manually flip through the paper file, which has been retrieved from the central files by the office assistant, to determine the purpose of the office visit and review the patient's relevant medical history.

A typical patient visit or patient encounter takes about 10 minutes, with the physical examination comprising about 2 to 5 minutes. Following the examination, or sometimes during, the clinician will make progress notes about the patient's medical condition, order any necessary tests, give the patient any prescriptions, and advise if follow-up appointments are needed. A clinician will usually spend about 2 to 5 minutes to make progress notes and place them in the patient file.

If tests are performed onsite, the clinician, laboratory technician or nurse, conducts the test. If the test results can be obtained relatively quickly, the clinician might wait for the results before releasing the patient, and review the results with the patient. Some testing, however, may be conducted off-site, and later reported to the clinician. The test results must then be analyzed and reported to the patient after the initial office visit, and follow-up appointments may be scheduled.

The amount of paperwork required has a significant impact on the service professional, which often detracts from the amount of time the service provider can spend with the patient. In the medical arena, every hour of emergency department patient care requires an hour of paperwork. For surgery and inpatient acute care, every hour of patient care results in 36 minutes of paperwork. In skilled nursing care, every hour of patient care results in 30 minutes of paperwork. And, in home health care, every hour of patient care results in 48 minutes of paperwork. A physician can spend 22-38% of his/her time charting on paper.

In today's practice, service professionals, and physicians in particular, have added restraints due to increased government and insurance regulations, liability, working longer hours, less time to spend with patients, all of which result in the practice being less profitable and providing a lower quality of care. Governmental and insurance rules and regulations include, for instance, electronic payment requirements, HIPAA (Health Insurance Portability and Accountability Act) requirements (such as electronic health transaction standards, unique identifiers, privacy and confidentiality standards, and security and electronic signature standards), coding and audit requirements, restricted formularies, clinical pathways, increased malpractice risks from pseudo standards of care and requirements for more structured data.

Accordingly, there is a need for a system that can reduce the amount of time spent by a clinician on activities outside the practice of medicine, such as paperwork, dictation, etc. There is also a need for a system that can reduce the amount of time spent by other workers in the clinician's practice including the administrative or office assistants, nurses, clinician assistant, and laboratory technicians. Those systems must also be able to comply with government and insurance regulations and must also provide data that can be analyzed to develop better care protocols.

Systems have been developed which automate patient tracking, medical documents or billing, such as described in U.S. Pat. Nos. 5,991,730, 5,991,729, 5,946,659, 5,933,809, and 5,899,998 to Lubin et al., Barry et al., Lancelot et al., Hunt et al. and McGauley et al., respectively. However, automated systems have not been well received by the service professional community, with fewer than about 5% of all physicians using some sort of electronic medical record (EMR) system, which is broadly understood to be a medical record system that has the capability to electronically provide all of the functionality and features provided by the paper chart, and data that can be analyzed to develop better care protocols.

Service professionals have resisted those systems since they are unable to keep up with the rapid pace and movement of the service professional during the various tasks which are performed throughout the day. One disadvantage of those systems is that they are technology-driven, as opposed to being user-driven, and therefore difficult to use, especially by those service professionals that have difficulty with computer technology.

In addition, those systems are fragmented in that they individually implement a single activity of practice management and managed care to manage scheduling, patient registration, insurance information, billing and collections. In instances where physicians are using EMR, practice management and managed care applications to manage their practices, the applications are typically stand-alone and run on disparate technology platforms.

The absence of a common technology platform requires multiple custom interfaces to connect the "silos" of information to work together in real-time. The process of developing interfaces between disparate applications by multiple vendors can be expensive and difficult and is usually costly and labor-intensive to maintain. Problems are time-consuming and difficult to identify when they arise. These usually costly and labor intensive interfaces are typically used by larger clinician practice groups (50 or more), integrated delivery networks, and university-based practices.

Consequently, those prior systems do not provide a single system that integrates the features of practice management, patient records and managed care. Further adding to the problem, those systems are not set up to communicate with each other, so that practices that have more than one system need to enter redundant information into each system. The various systems are not well suited for interaction between each other, or to maintain information that would be useful to the other systems.

However, even if those fragmented systems could communicate with one another, the systems would merely be interfaced, as opposed to being integrated. Systems that are interfaced exchange limited data to address practice management, EMR and managed care needs. Interfacing systems also require multi-vendor support and the sharing of limited data across limited system components and multiple databases. Interfacing also leads to inconsistency in system user interfaces and system versioning is difficult to manage.

SUMMARY OF THE INVENTION

Accordingly, it is an object of the invention to provide a medical software system that integrates all aspects of practice management and managed care, including schedule management, patient registration, insurance information, and billing and collections, with the EMR. It is another object of the invention to provide a practice management system which is secure, has functionality and usability, tracks work flow of service professional, and makes the best use of manual resources. It is yet another object of the invention to provide a practice management system which is cost effective to implement and maintain, even for small practice groups (2-5 clinicians), but yet configurable to meet the needs of various specialties.

In accordance with these and other objectives, a medical management system is provided that integrates all aspects of healthcare provider practice management and managed care, including schedule management, patient registration, insurance information, and billing and collections, with the EMR. The system integrates a central framework module, a scheduling module, a registration module, an account management module and an electronic record module to provide a seamless exchange of information.

A clinical module provides an administration builder which allows users to define a customized template. The templates are used by a document builder to generate documents, such as progress notes and H&P Notes, which are retained in the patient's electronic chart. The progress note template allows the clinician to record a patient encounter by presenting the clinician with predefined sections and sentences that are easily completed by the clinician during or after the patient encounter. The templates and documents generated are designed to closely resemble a paper chart. Information gathered during patient scheduling, registration, triage, and previous encounters are referenced to pre-populate the templates to avoid having the clinician entering redundant information. The documents are relied upon to automatically generate charges, from which electronic requests are sent to a claims clearinghouse.

The system results in increased revenue due to coding accuracy, billing and fee schedule cross referencing to reduce under-payments and over-payments, writeoffs, improved clinician productivity, improved claims management and payment reconciliation of under payments, patient care reminders that generate preventive/preventative care visits, and improved receivables collections. The system results in a reduction of cost, such as a reduction in the cost of copying and storing documents and records, malpractice insurance premiums, transcription costs, paper and related supplies, rejected claims and costs associated with claims reprocessing, labor savings due to efficiencies and resulting in possible staff reduction or redeployment, and decreased repeated lab tests.

The system has intangible clinical advantages, such as improved quality of patient care through the provision of preventive/preventative care, improved chart availability, drug/allergy interaction alerts, outcomes analysis, improved response time for patient information requests, improved clinician and administrator satisfaction, reduction in paperwork and increased available time to spend with patients. Intangible business benefits include more efficient scheduling and appointment notification, avoidance of misplaced or lost patient record files, elimination of redundant data management, improved financial accounting accuracy and reporting, and increased market share. The system is efficient with respect to chart pulls, referral coordination, billing documentation compliance, coding compliance and lab report filing.

BRIEF DESCRIPTION OF THE FIGURES

FIGS. 12, 13 and 14 show the account information, charges and contracts/fee schedule screens of the AR module of FIG. 6;

FIG. 16 is the template administration screen of the clinical module 30;

FIGS. 17-27 show template administration screens used to define a template;

Figure 31:
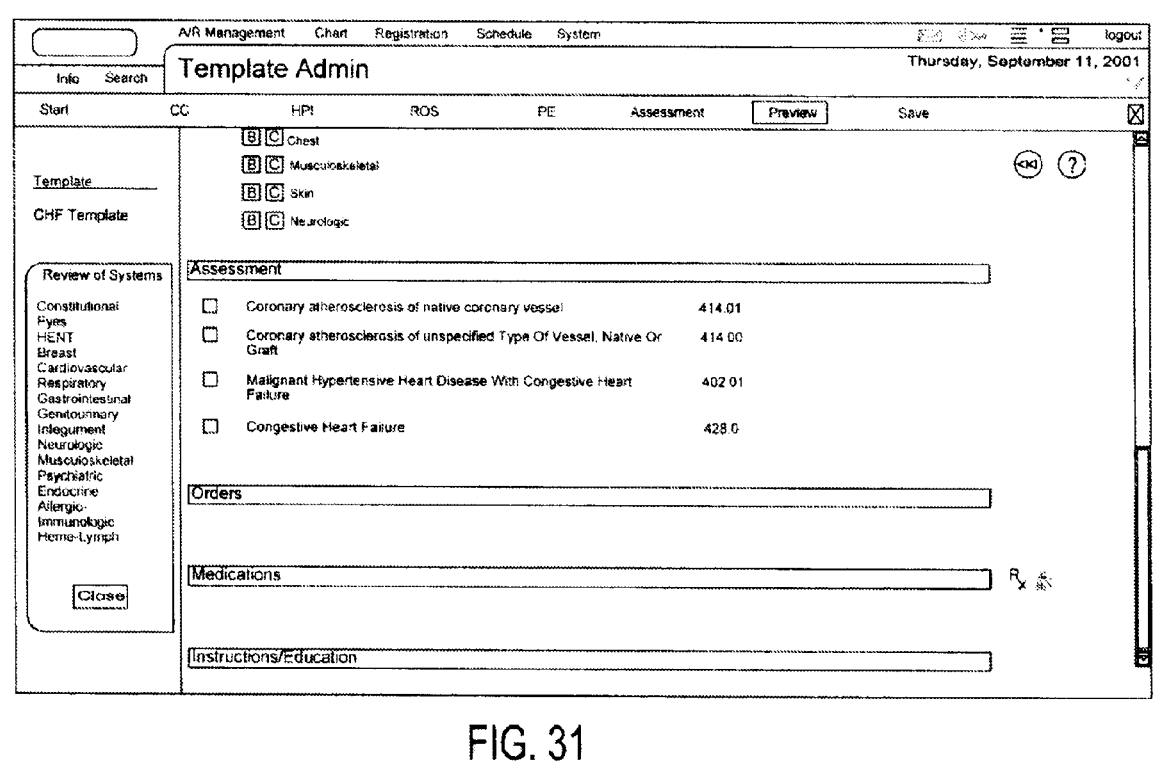

FIGS. 28-32 show the preview option during the template administration;

FIGS. 33-36 show document building screens used to build a document in accordance with a template;

FIGS. 37-38 show a Progress Note document which was generated in accordance with a Progress Note document building template;

FIG. 39 shows list of documents in a patient's chart; and,

FIG. 40 shows an H&P note being completed in accordance with an H&P Note document building template.

DETAILED DESCRIPTION OF THE PREFERRED EMBODIMENTS

Figure 1:
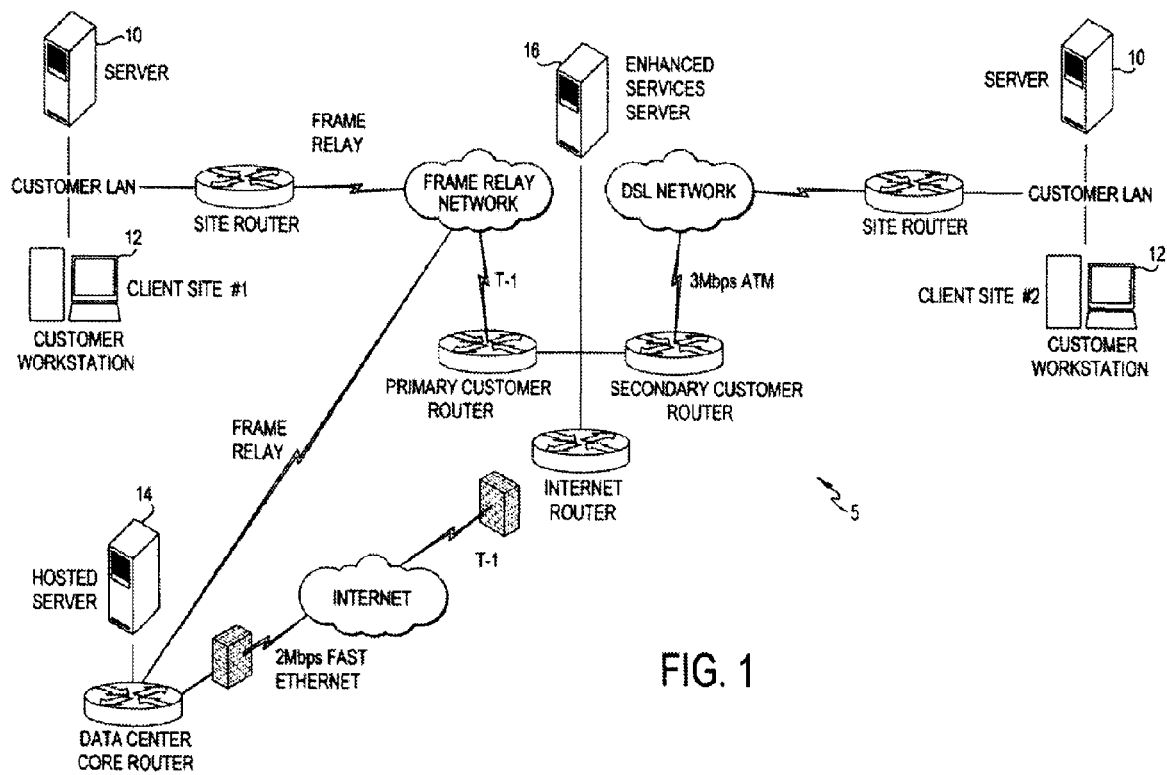
FIG. 1 shows the overall network architecture in accordance with the preferred embodiment of the invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose.

The present invention delivers an ambulatory software suite that integrates practice management, electronic medical records ("EMR") (i.e., patient records) and managed care functionality. An ambulatory suite is a group of applications that is designed to meet all the needs of a practice. These applications are built on the same architecture and are designed to share information seamlessly based on integration rather than interfacing.

The system integrates, as opposed to interfacing, all aspects of a clinician's practice, namely the clinical, financial and administrative processes. Integration provides a single vendor solution that addresses all practice management, EMR and managed care needs. It also allows for single vendor support and the sharing of all data across all system components through a single database which avoids errors, duplication of data entry and inconsistency of information. For instance, scheduling and registration data flows to billing; registration data flows to the patient's chart; coding, scheduling and prescription data flows from the chart to billing, to the schedule and to the pharmacy, respectively.

A single integrated system also completes patient tracking which facilitates cost accounting analysis, provides consistency in all system user interfaces and allows for greater security and audit trails. In addition, system administration of all the applications can be handled through a single system administration feature. An integrated system also means only a single vendor, which eliminates the need for interface management, and that the system can be upgraded as a single entity with consideration of all functionality that may be affected.

The EMR is characterized as having a direct data entry into a patient's record of all information that currently can be entered into a paper record. The EMR is a customizable and organized storage of information, and provides a comprehensive aggregation of content for a single provider or location for each patient. In addition, the EMR is capable of incorporating information from outside sources, such as through document scanning, and has information mobility, accessibility and reviewability.

System Architecture

Turning to the drawings, FIG. 1 shows the overall system 5 in accordance with the preferred embodiment of the invention. The system 5 has two primary elements: a main services server 10 and customer workstations 12. Optionally, the main services server may be hosted at a data center (server 14) as opposed to being hosted at the practice location. The main services server 10 is at the center of the system 5, and is located at a central location for communication with each of the customer workstations 12.

The main services server 10 contains all of the system applications and controls operation of the system 5. The main services server 10 includes the overall framework module 20 (FIG. 5), the AR (accounts receivable) module 30 (FIG. 6), the clinical module 40 (FIG. 7) and the scheduling module 23. The main services server 10 controls the communication of the system 5, stores data, and controls the various operations and processes.

The customer workstations 12 are located at various locations, remote from the main services server 10, throughout the clinician's office(s). The customer workstations 12 are part of a Local Area Network ("LAN"). The workstations 12 form the point of communication between the customer and the main services server 10. When the customer workstation 12 is located at an office remote from the main services server 10, the customer workstation 12 preferably communicates with the main services server 10 through a customer router which is accessed via a DSL ("Digital Subscriber Line") network or frame relay network, and a site router. The site router is located with the customer workstation 12 and the main services server 10 at the customer's location, and the customer routers are located at a central location with an enhanced services server 16.

When the main services server 10 is hosted at a designated data center, that hosted server 14 communicates with the customer workstation 12 through a customer router, via the frame relay network or DSL network, and a data center core router. The enhanced services server 16 also controls an Internet router used to provide access from the clinician office to the Internet for email and web surfing capabilities. The Internet router is located behind a firewall to provide security.

The system 5 has features addressing each of the HIPAA Security Regulation's requirements, including biometric login, restricted access based on login authorization (i.e., individual charts or chart sections), audit of who looked at what section of a chart and when, and the restricted ability to copy, print, fax, email and export information based on login authority. The system also has functionality to assist in compliance with the HIPAA Privacy Regulations, such as consent tracking and disclosure logging functionalities. The system also supports EDI standards, including transactions, code sets, and identifiers.

With respect to communications capabilities, HL7 (Health Level 7) compliant messages are fully supported and allow for inbound and outbound data communications with most healthcare information systems. Thus, the system interfaces with other related systems, such as hospital information systems, such as HBOC, Meditech, and Cerner. These hospital information systems manage electronic data for hospitals and the system exchanges information such as patient demographics, processing pre-certifications, orders, results. The system also interfaces with diagnostic equipment lab systems to exchange information. Transactional information and data associated with ADT (Admissions, Discharge, and Transfer), orders, results, labs, prescriptions and other data types can be efficiently shared.

The system also handles non-HL7 messages for data exchange between claims processors, diagnostic equipment and other medical information systems. All messages are designed with current industry standards and the proposed/final HIPAA regulations in mind. Messaging requiring more programmatic integration, as opposed to data exchange interfacing, can be pursued through XML-based programming.

The system 5 preferably uses Microsoft's Digital Dashboard web-browser interface, Microsoft Windows 2000, Microsoft SQL Server 2000 database and the Windows Distributed interNet Applications (DNA) technologies. The system's support for the HL7 data exchange standards and the X12N (Insurance Subcommittee of Accredited Standards Committee X12) EDI (Electronic Data Interchange) standards facilitate both systematic and data-level integration, with X12 particularly supporting claims processing and electronic remittance advice. Additionally, use of XML (Extensible Markup Language) provides for enhanced functionality within a browser environment and facilitates extensive interface configuration, such as with pharmacy or prescription systems, healthcare research information, handheld devices and medical supplies ordering.

The system integrates the Unicor Alpha II coding database, the First DataBank drug interaction database and the SNOMED controlled medical vocabulary database. These databases provide unique functionality and are provided as a "back-end" content repository which is maintained as part of the overall system 5. The SNOMED medical vocabulary database is optional, and need not be provided.

The customer workstation 12 is implemented in single technology platform—a browser, making use of a web-based, as opposed to web-enabled, development approach. The browser facilitates remote access to all practice and patient information within a highly secured environment, and enables communication between clinicians and their patients. The browser also enables a single source of support, to thereby minimize the cost of ongoing system maintenance. The browser also enables a scalable solution that can be expanded from smaller clinician practices to larger healthcare communities, and can be delivered to a targeted group of clinician specialties. The system also includes a website that can be hosted as a service from an application service provider, or deployed onsite at the clinician's office.

The system 5 employs a central service, which is a utility that runs in the background and automates tasks. It uses an event driven design to perform tasks, wherein an event can be a file that is empty, have a single line or a data file. The service monitors a set of directories on the server and looks for the presence of an event or flag file to initiate a script or application. The flag files indicate what action to perform. The central processor of main services server 10 manages the launching of script files to control operation. Multiple scripts and flags can be used together to complete tasks, and each task may consist of multiple scripts and/or third party programs.

The central service uses two types of utilities, one that runs on the base and one that runs on the main services server 10.

The clinician preferably uses a highly graphical and configurable interface which is implemented with a stylus and lightweight, mobile pentop input device. The office administrator also interfaces with a browser interface which enables rapid data entry and retrieval. All the user interfaces communicate with the customer workstation 12.

The main services server 10 includes a data repository. The repository uses relational database technology to manage all discrete data centrally, which facilitates the sharing of information across all areas of the system. This functionality reduces the potential for redundant data entry and data storage.

The system network 5 allows clinicians to collect patient outcome results and correlate those results with treatment plans to measure effectiveness. That information can be exchanged with data from other clinicians, research institutes, universities and pharmaceutical companies for broad-based ongoing research. Data is aggregated from each participating clinician's EMR module into a centralized repository which is maintained by the enhanced services server 16, with appropriate de-identification performed to protect patient privacy. A controlled medical vocabulary is enforced to normalize the collected data. Access to the repository is controlled to certain biomedical informatics researchers, who can use query tools to mine the data.

The network 5 allows the clinician to submit claims directly through the network to payors, eliminating clearinghouse costs and delays, or through a clearinghouse, taking advantage of clearinghouse edits and support. The network 5 can further be used to aggregate the purchasing of supplies, goods and services by clinicians and patients.

Figure 2:
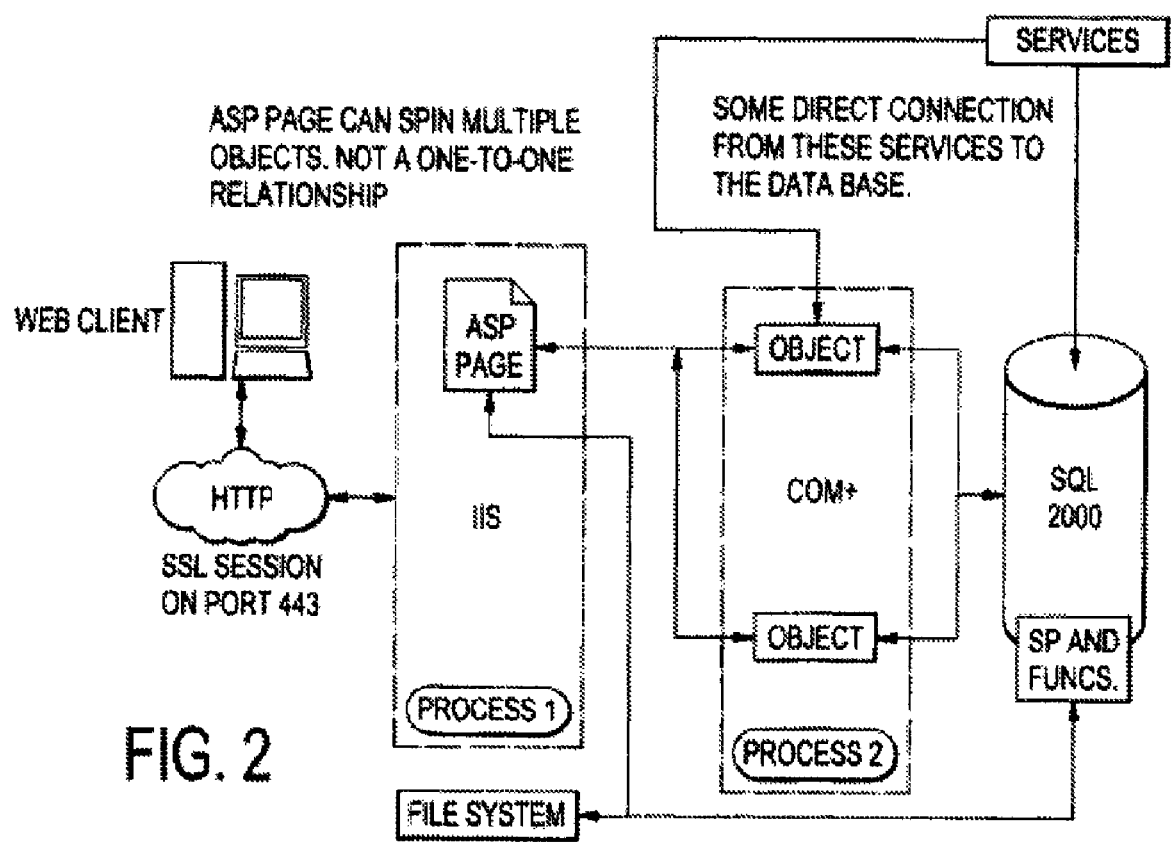
FIG. 2 shows the system architecture of the main services server 10 of FIG. 1.

FIG. 2 shows the system architecture from an applications standpoint. FIG. 2 represents the internal workings of the main services server 10 of FIG. 1. The services represent a series of Windows 2000 Service programs that support and enhance the functionality of the MTS COM+ middle-tier and to provide operating system capabilities to the product as a whole. SP (Stored Procedures) and Functions are two different ways of storing source code in the database. Processes can be supported at either the IIS server or the COM+ server.

Figure 3:
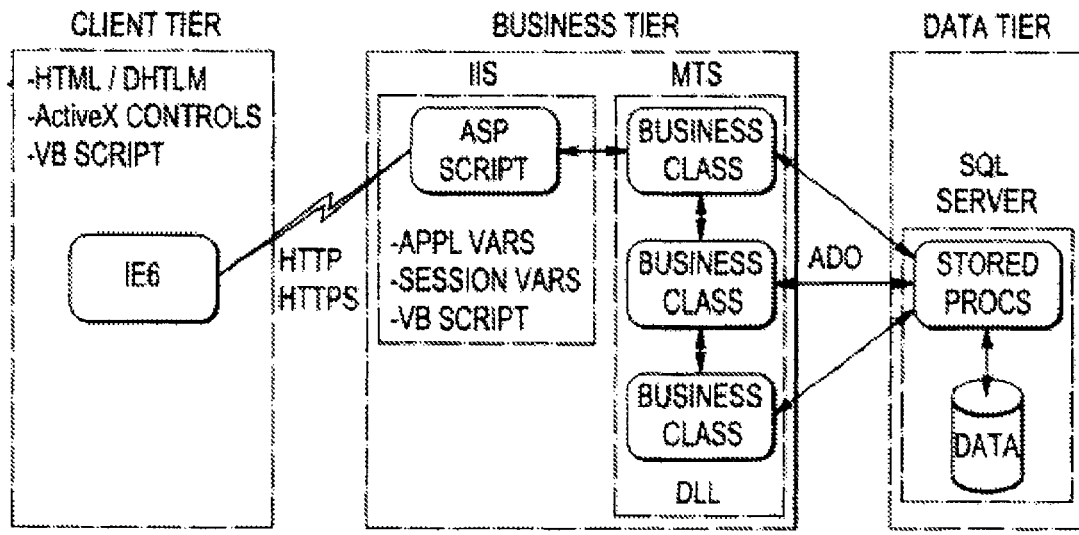
FIGS. 3 and 4 show the preferred architecture of the main services server 10 and workstation 12, as having a client tier, business tier and data tier.

FIG. 3 shows the preferred architecture of the main services server 10 and workstation 12, as having a client tier, business tier and data tier. Both the data tier and the business tier are located on the main services server 10 and the client tier is located on the customer workstation 12. The architecture is based on Microsoft Distributed Internet Applications ("DNA") architecture using COM+ middle-tier objects for business rules and Microsoft Transaction Server ("MTS") transactions for resilient database storage and retrieval. A standard n-tier design model provides separation of the detailed practice management business rules from the data storage and client presentation.

The client tier targets Microsoft's Internet Explorer 6 as the client platform. The business tier is implemented on Microsoft Windows 2000 server using the Microsoft Internet Information Server ("IIS"), Microsoft Active Server Page ("ASP") technology, Microsoft Transaction Server ("MTS"), and COM+ middle-tier objects. The data tier makes use of Microsoft SQL*Server 2000. The IIS tier provides for handling the robust, interactive client needs of the product. The MTS COM+ middle-tier provides for a centralization of business logic and routines. The SQL*Server Database tier focuses on data storage and aggregation. The IIS, COM+ and SQL*Server are also shown in FIG. 2.

Figure 4:
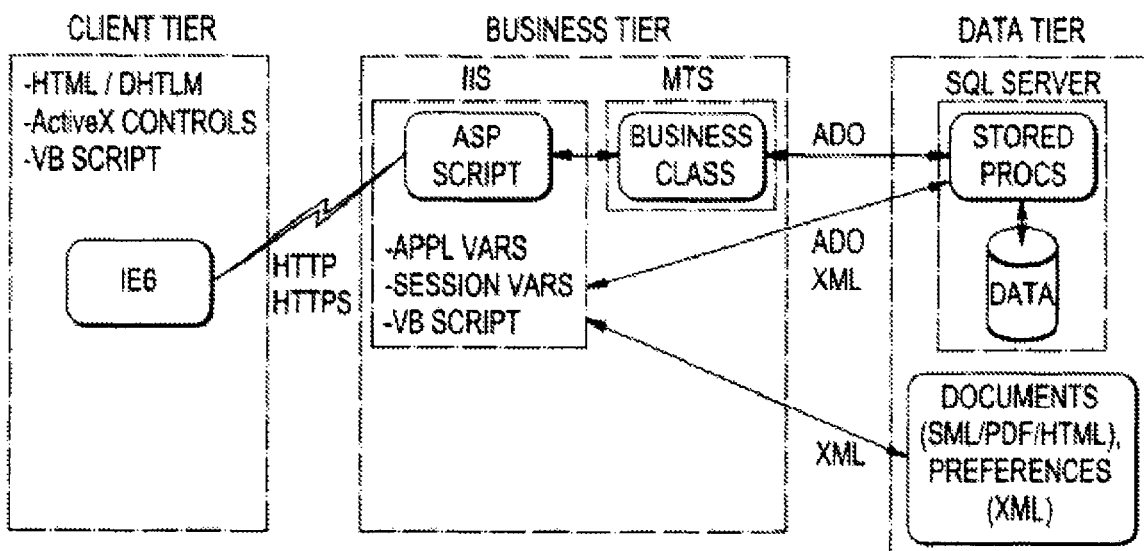

FIG. 4 shows another preferred architecture of the main services server 10 and workstation 12, as having a client tier, business tier and data tier. FIG. 4 makes use of all the benefits of FIG. 3, but extends the model to make use of current Microsoft XML-based Internet architecture designs to provide an interactive client experience. A standard web Internet design model provides for tighter integration of the customization of business logic and the web browser presentation, which is extended with Microsoft Internet technologies XML and VB scripting classes.

The client tier uses Microsoft Internet Explorer 6 as the client platform. The business tier is implemented on Microsoft's Windows 2000 Server using IIS, ASP and native XML communication and handling capabilities. The data tier primarily stores data in XML files so that data, content and context can be stored together in a meaningful way. It also makes use of Microsoft SQL*Server 2000 to provide for fast, easy system access to list-driven data storage, using XML-SQL functionality and enhanced functions capabilities.

The data tier in this model also makes use of the File System for storage of clinical documents and user customizations. Using the File System to store clinical documents improves the speed of the system because once a clinical document is signed, it is always referenced as a view-only document. The web architecture lends itself well to the transfer of documents.

Main Services Server

Figure 5:
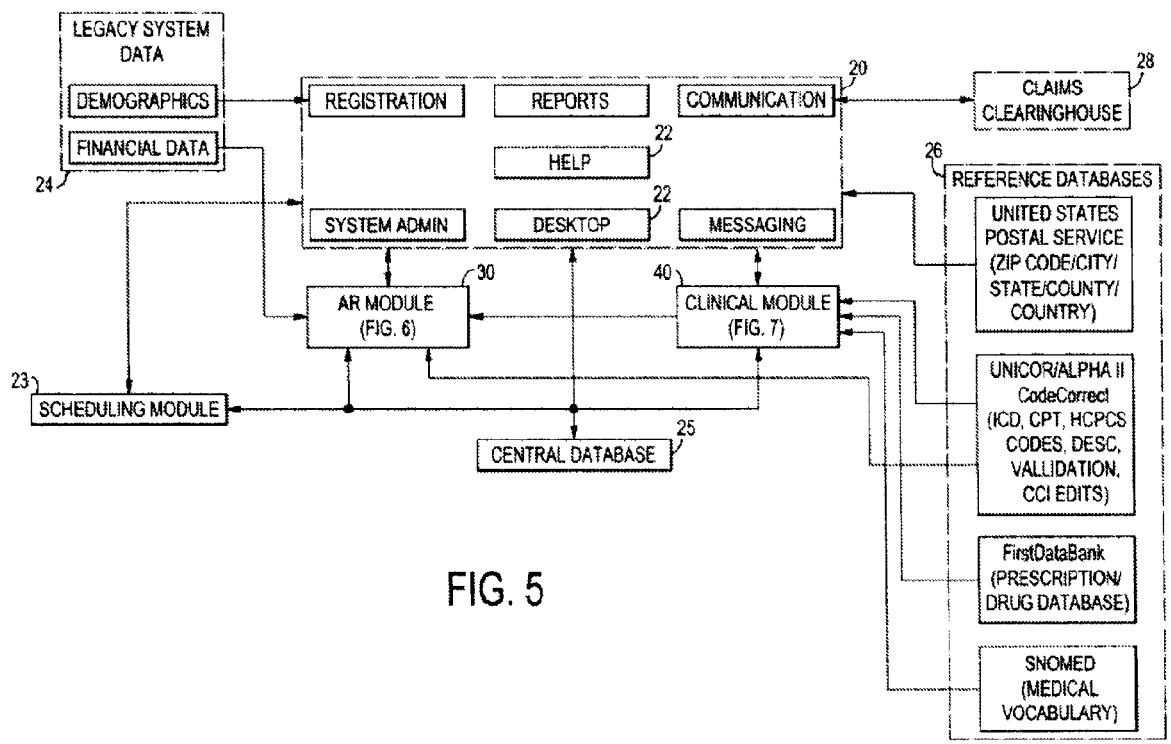
FIG. 5 is a block diagram detailing the functional makeup of the system, with each module implementing the client, business (middle), and data tiers.

An overview of the main services server 10 structure is shown in FIG. 5. The main services server 10 has a framework module 20 with various components 22, reference databases 26, scheduling module 23, AR module 30 and clinical module 40. The clinical documentation of the EMR is handled by the clinical module 40. FIG. 5 shows the functional makeup of the system. Each module has pieces of code implementing the client, business (middle), and data tiers. A majority of the EMR interaction is done through robust client-side interaction with the customer workstation 12, but is centrally processed, stored, and managed by the main server 10. The main services server 10 is also capable of receiving patient demographic and financial information from legacy systems 24 by way of migration utilities that import that information into the main services server 10 database.

The main services server 10 communicates with a claims clearinghouse 28 for processing insurance claims. The AR module 30 is shown in further detail in FIG. 6 and the clinical module 40 is shown in further detail in FIG. 7. The main services server 10 has a centralized framework module 20 that supports communication between the various components 22, the scheduling module 23, the AR module 30, the clinical module 40 and the legacy system and reference databases 24, 26.

A central database 25 is provided that is used to store data for each of the framework module 20, the various components 22, the scheduling module 23, AR module 30 and clinical module 40. As used herein, patient data generally refers to demographic, financial and clinical information. Clinical information includes symptom, observation, treatment, assessment, diagnostic and therapeutic information. The central database 25 ensures that all information used by the system is retrieved and stored at the same location, to avoid users having to enter redundant information and ensure that all areas have access to the most current information.

The scheduling module 23, the AR module 30 and the clinical module 40 are separate and distinct modules, but are fully integrated through the use of shared functionality in the framework module 20, such as the desktop, registration, reports, audit logging, security, system setup, user preferences, alerts and reminders, and messaging. The main services server 10 provides seamless integration between the framework module 20, the scheduling module 23, the AR module 30 and the clinical module 40, as well as other ancillary components, including the central website portal, centralized messaging, email, and protected Internet access. The framework module 20 preferably has components 22 which include registration, reports, system administration, communication, help, messaging and desktop.

FIG. 5 represents integration of each stage of a clinician's practice, including scheduling, registration, charting, AR management and reporting. The system automates each of the processes associated with a clinician's practice, from patient scheduling, to the clinical encounter, though the process of filing claims and receiving payments. Information collected within one area of the system flows together to facilitate a workflow process at another area of the system.

For instance, information is collected throughout the patient registration, and is used by billing to initiate the coding and billing processes. The integrated system reduces the administrative burden, allowing more time to spend with patients, streamlining the claims process and improving coding and the financial accuracy associated with the billing process and ultimately maximizing the practice profitability.

On the financial end, the system integrates coding and billing, fee schedule management, patient statements, AR management, collections electronic remittance advice and reporting. AR management includes, for instance, electronic charge tickets, balance tracking, charges, payments and adjustments, claims processing, claims maintenance, electronic remittance, contracts and fee schedules, insurance plans, and statements. Coding and billing includes, for instance, automation to facilitate coding and documentation compliance, as well as fee contract analysis. This assists managers in their effort to eliminate the occurrence of undercoding, reduce the risk associated with potential overcoding and identify instances of under-payment to maximize profits and reduce coding liability.

Thus, the system handles point-of-care charting, such as document management, point and click document generation, evaluation and management ("E&M") coding assistance, summary lists, prescription management, orders and results and flowsheets. On the clinical side, the system integrates point of care charting, discrete data storage, clinical reminders, laboratories and prescriptions, documentation compliance, coding assistance, order management and reporting.

On the administrative side, the system integrates patient scheduling, patient reminders and alerts, desktop, registration, insurance eligibility, visit check-in and check-out, reporting, audit logging, security, system setup, user preferences, and messaging.

Registration

The framework module 20 of the main services server 10 has a registration component 22 which includes visit check-in 33 to capture demographic, insurance coverage and administrative information for each patient. The information in the registration component 22 can be entered by the practice staff. However, the information can also be entered by the patient through a secure Internet link or at a waiting room kiosk through an interface with the customer workstation 12. Required fields, patient flags and checklist procedures ensure thorough information collection for new patients and prompt the user to ensure that the existing patient information is kept current.

The registration component 22 supports patient registration, including new patient information and access to patient demographic information from any prior management system which has been imported from a legacy system 24. The registration component 22 stores any information obtained for new patients and information modified for existing patients, including both demographic and insurance coverage information. Registration usually takes place after the patient has scheduled an appointment, but the system will allow registration without a scheduled appointment, which is useful for physician practices that accept walk-in patients.

The information retained by the registration component 22 can be used by any other component 22, as well as the scheduling module 23, the AR module 30 and the clinical module 40. Likewise, the other components 22, the scheduling module 23, the AR module 30 and the clinical module 40 sometimes receive new or updated information that is then stored by the registration component 22. In this manner, the main services server 10 has a single source of registration information that is used systemwide, so that users need not enter information that has been previously stored at one module when working in another module. In addition, the registration information is always kept current for all modules.

The registration component 22 can also receive patient data from a prior management system, e.g., a legacy system database 24. The information in the legacy system database 24 is imported from a prior management system, either through manual entry or by conversion of electronic information. The registration information imported from the legacy system database 24 may include demographic information about the patient, such as name, address, date of birth, social security number, insurance coverage, and sex. The legacy system database 24 may also include financial data, such as outstanding balance, account information, and insurance claims being processed. The system 5 also allows for the import of financial information into the AR module via a financial migration utility.

Visit-specific information, such as financial responsibility and third party insurance coverage is also captured. The information is made available to other components of the system, such as for charts and billing to eliminate redundant data entry and management. The system includes patient identification and record retrieval by digital photo, which allows personal treatment of the patient as well as positive identification to prevent insurance fraud.

The desktop 22 displays the check-in and check-out status of patients and supports unscheduled patients and can launch a patient's chart. The system displays the present day schedule, as well as open visits from prior days. If the user selects another date, the visits and scheduled appointments for that selected date are displayed.

The system registration allows users to associate one or more insurance plans with an employer. Users may set up information about local employers for association with patients and persons. This functionality greatly speeds up the process of entering insurance information for a specific patient. Instead of entering detailed insurance information for every patient, using this functionality, a user can quickly capture a patient's insurance information by associating a patient with a specific employer insurance plan that has already been entered into the system. Thus, insurance plan maintenance or the addition of new plans can be performed for a patient's record while accessing the patient's registration information.

Figure 8:
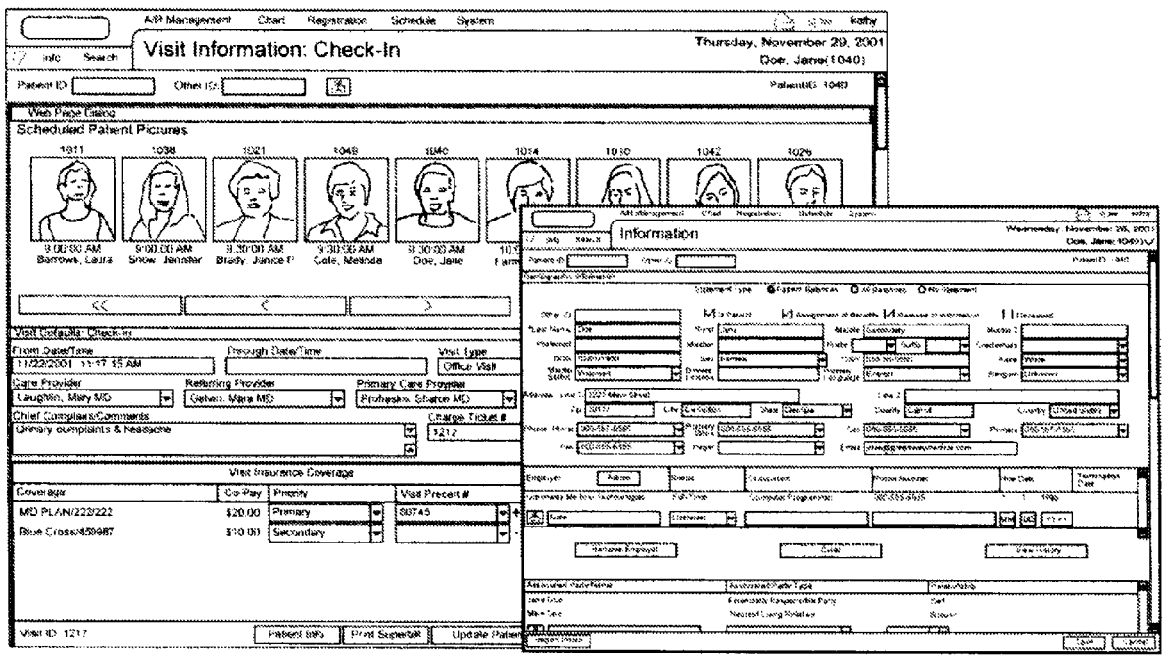
FIG. 8 shows the visit information check-in screen and patient registration information screen of the registration component of FIG. 5.

In the example shown in FIG. 8, the user has entered all of a patient's demographic and insurance coverage information into the system, including all of the CMS (Centers for Medicare & Medicaid Services—formerly HCFA, the Health Care Financing Administration) required data, as well as other useful information such as e-mail address and the patient's digital photo. Once the patient information is entered, the user is ready to check the patient in. Additionally, from the visit check-in screen, the user can easily see important information about the patient, such as referral management information, payment collections notices and co-pay arrangements. The system automates the prior approval for referrals, admissions, orders, procedures, special medications, and other items requiring prior approval.

The visit information component 33 is primarily used to track a patient's office visit. In preparation for the visit, the visit information sub-section 34 obtains information from the scheduling module 23, namely Date of Service, Time of Service, providers, and location. That information is used to pre-populate the user's check-in screen and the user can fill in any missing information.

The user may also input pre-certification information from the insurance company or from the patient at check-in, if that information has not been previously obtained and entered into the scheduling module 23 or if that information has changed since the patient made the appointment. The user also obtains information from the patient regarding the purpose for the visit, if that information has not been previously obtained and entered into the scheduling module 23. The visit information, however, is not used to update the scheduling module 23, but rather any changes to the appointment information is retained for historical/tracking purposes.

Scheduling

The scheduling module 23 of the main services server framework module 20 supports scheduling for patients, clinicians, staff members, office equipment, or any resource the user chooses to define. Scheduling is a rules-based, flexible module that supports many different levels of scheduling complexity. Appointment scheduling is administered using automated scheduling rules that ensure proper resource and time allocation, and further facilitates a smooth flow of patient appointments. Appointment scheduling is configurable to the practice and to the user. The user can review schedules at any time from any point in the office, providing the office assistant with real-time appointment availability information, and providing the clinician with real-time scheduling information.

Users can schedule patient visits using simple "drag and drop" techniques in accordance with personnel, resource and equipment availability. It provides appointment reminders and alerts to minimize errors, allows for more efficient processing of appointments and ensures that patients are properly prepared for their visits. Patient flags, such as In Collections, Disabled Patient, and History of Missed Appointments, can be associated with a patient to serve as reminders to make special arrangements for a specific patient when scheduling an appointment.

As an appointment is scheduled, all resources, such as facilities, equipment, personnel and medical procedures, are taken into consideration to ensure that conflicts do not occur between resources. Rules templates can be defined to control the available appointment times for resources. Templates may be defined and applied across many resources and dates to minimize schedule maintenance. The resources are presented to the user with several viewing options, such as viewing multiple providers' schedules on the same day or multiple days for one provider.

The user can perform advanced searches for multiple resources and various time and date ranges. Once search parameters have been defined and saved, the user may access the saved search template for future use. The next available appointments are quickly accessible and displayed to facilitate an efficient scheduling process. The appointment scheduling reduces patient scheduling conflicts.

Figure 9:
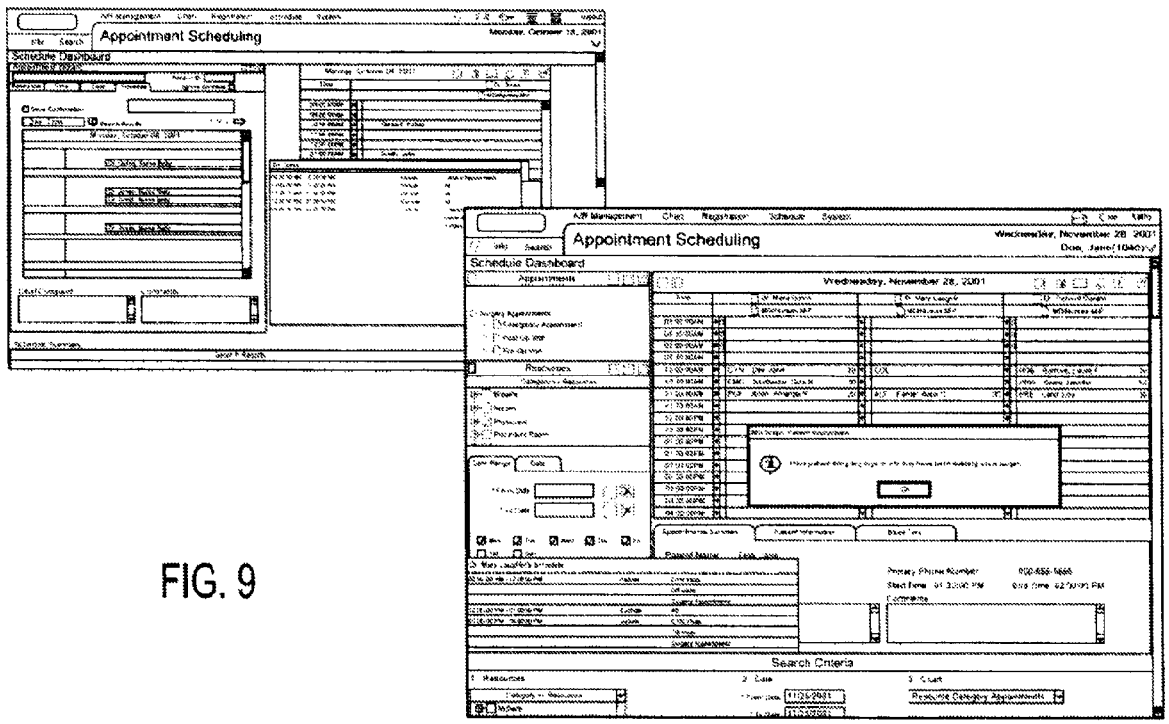
FIG. 9 shows the appointment scheduling screen of the scheduling module of FIG. 5.

In the example shown in FIG. 9, the user has scheduled an appointment, and the system automatically alerts the user to remind the patient of specific instructions to follow prior to the appointment. The instructions are based upon the type of appointment that has been scheduled for the patient. Additionally, as the user attempted to schedule the appointment, the system indicated that a rule existed for that type of appointment, which the user then chose to view the rules.

Reports

The reports component 22 supports all reports. The system has a standard set of reports to meet user needs which users can display, filter and sort. Multiple filter and sort options can be saved as configured reports for future reference. This standard report set with its customizing options allows users to report on almost any combination of data within the system database, which manages administrative, clinical and financial patient data. The user selects the report criteria, such as insurance company, insurance plan, billable provider, and the report is generated.

In addition to the standard reports, a report writer allows the user to modify and save existing standard reports. A user-defined reporting tool is provided which provides a number of pre-defined datasets which the user can choose any fields from to create a customized report. Reports can be run immediately, or in the background, sending a notice to the user via the messaging system when the report is ready to view.

Reports can be generated as needed, as well as daily, weekly, monthly, or annually. Reports can be for any date or date range and can be sorted by many different parameters, such as provider, practice, insurance plan, and patient. Once the report is generated, it can be printed, and exported to a variety of other file formats, such as Microsoft Word and Excel, for incorporation in office documents.

Examples of the standard reports include: Patient Financial, such as Account Information Report; Demographic Information, such as Patient Information Sheet; Provider Productivity Analysis, such as Summary By Provider, Procedure Code Analysis Report, and Adjustment Analysis Report; Practice Statistics, such as Procedure Code Analysis Report; Referral Information, such as Referring Provider Analysis Report; Scheduling Status, such as Appointment History Report, and Daily Scheduling Report; Delinquent Accounts, such as Collection Balance Report, and Aging Account Summary Report; Insurance Claims Reporting, such as Claims Analysis Report; Audit Report, such as Audit Log Report (HIPAA Security Requirement), and Disclosure Log Report (HIPAA Privacy Requirement); Managed Care Reporting; Contract Analysis; Delinquent Accounts; Insurance Claims Reporting; and Accounting Reports, such as Account Information Report, A/R Balancing Log Balance Tracking Report, and Transaction Detail Report.

Administration/Communication/Help/Reference Databases

The system administration component 22 supports all administrative functions, such as setting user passwords, system/user settings, and controlling access. Administration is implemented, for instance, at the AR administration component 31 of the AR module 30 (see FIG. 6).

The communication component 22 supports all the external communication for the system 5, including communication with the claims clearinghouses 28. The help component 22 provides user support information for all the modules. The messaging component 22 controls internal messaging.

The reference databases 26 maintain all reference information that is needed for the main services server 10. As shown in FIG. 5, the reference databases 26 include, for instance, postal information, insurance codes, drug information and a medical vocabulary such as SNOMED (Systematized Nomenclature of Medicine). The postal information includes information on zip code, city, state, county and country. The insurance codes stored in the reference database 26 include insurance rules and regulations, such as ICD (International Code of Diseases), CPT (Current Procedural Terminology), HCPCS (HCFA Common Procedure Coding System) codes, and CCI (Correct Coding Initiative) edits. The CCI edits dictate which CPT code combinations and which ICD-9 codes are valid to support certain CPT codes in order to be valid for payment of a Medicare claim.

Desktop

Figure 10:
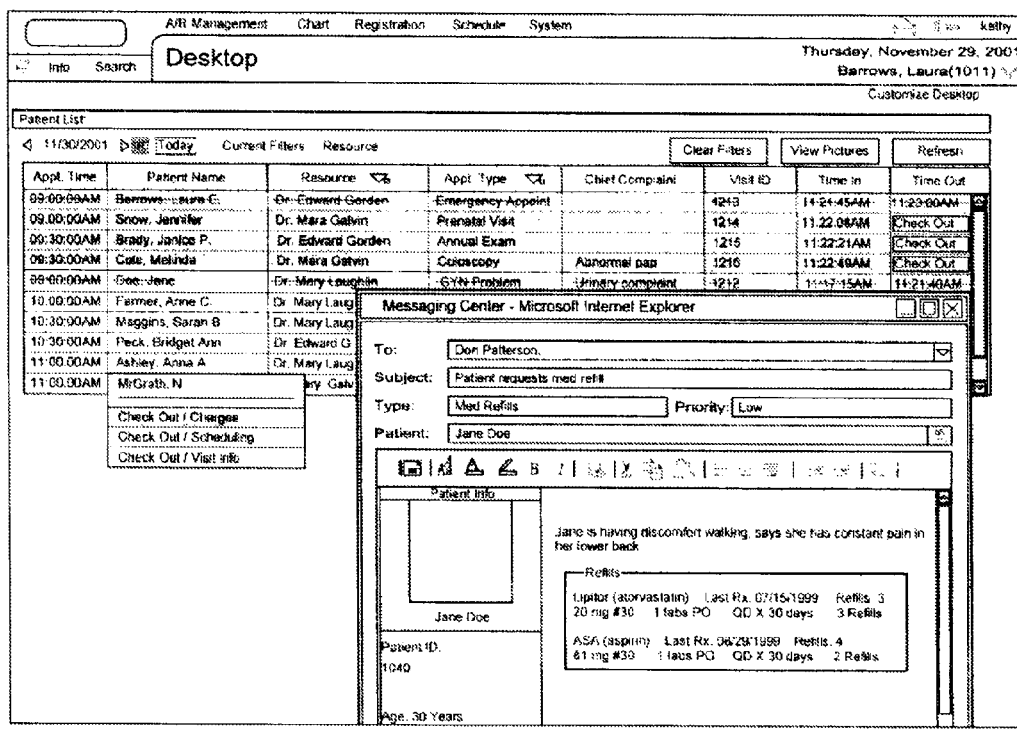
FIG. 10 shows the desktop and internal messaging supported by the framework module 20 of FIG. 5.

Turning to FIG. 10, the desktop is shown, which is supported by the desktop component 22 of the framework module 20. The desktop is the main user interface which allows centralized access to each component within the application. The desktop is presented to the user at a user input device, which can be a wireless pentop or personal computer that is in communication with the user's workstation 12. The desktop is configurable to the individual user's needs and preferences, to help users organize daily workflow and tasks. Users can view and filter scheduled patients and walk-in patients, and have access to internal messaging and external applications such as stock quotes, web access and educational resources.

Figure 6:
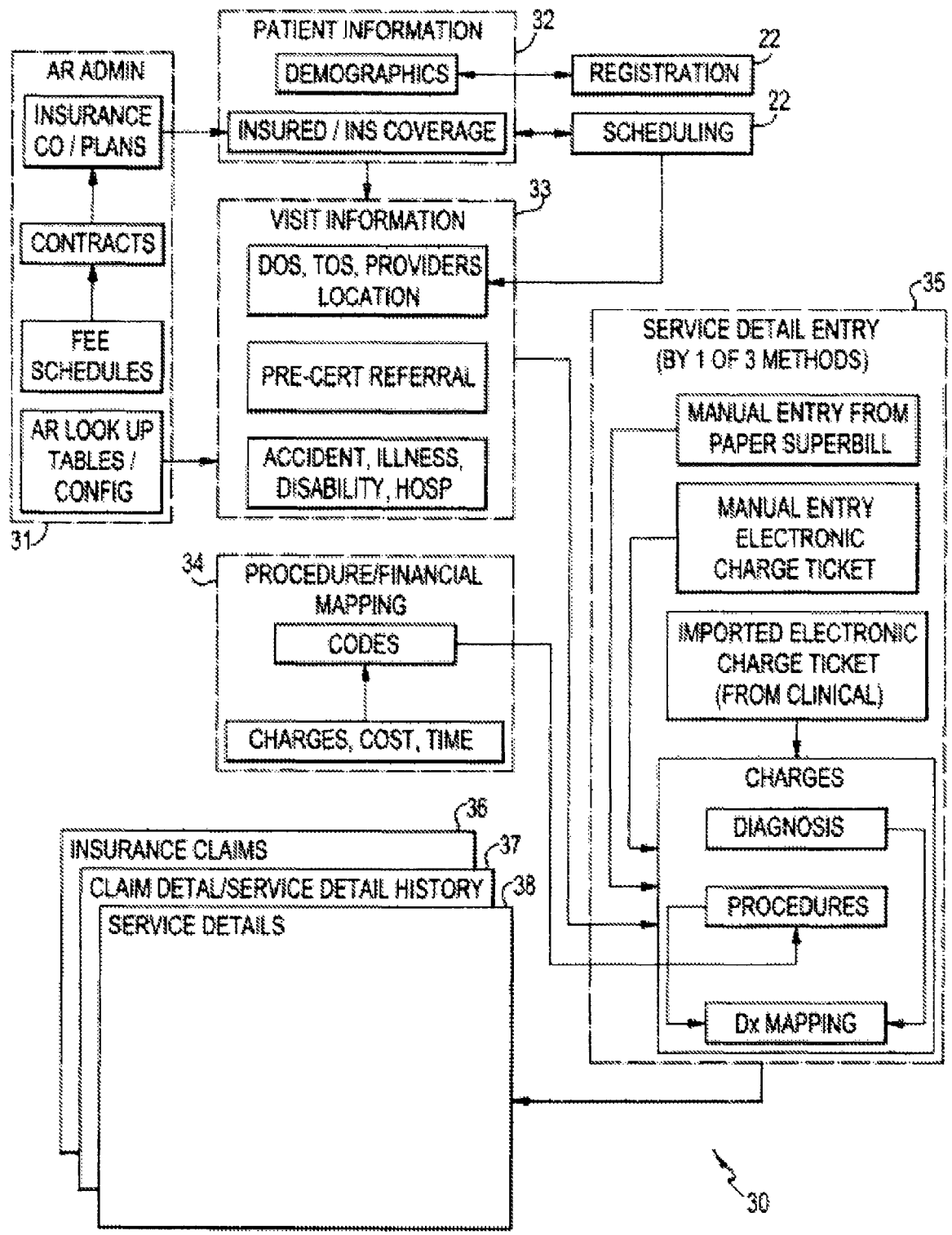
FIG. 6 is a block diagram of the AR module 30 of FIG. 5.

A menu bar is located at the top of the desktop, with the options of AR management, chart, registration, schedule and system. The menu bar has a pull-down menu that allows the user to select the type of operations to be performed. AR management is supported by the AR module 30 (FIG. 6). The user can check a patient's account information, charges, or e-charge ticket; or check payments and adjustments such as patient transactions and insurance transactions; or check claims, such as claim maintenance, claim processing and claim status; or check system setup such as AR configuration, lookup tables, contracts/fee schedules, e-charge ticket configuration, insurance plans, procedures and statements.

Figure 7:
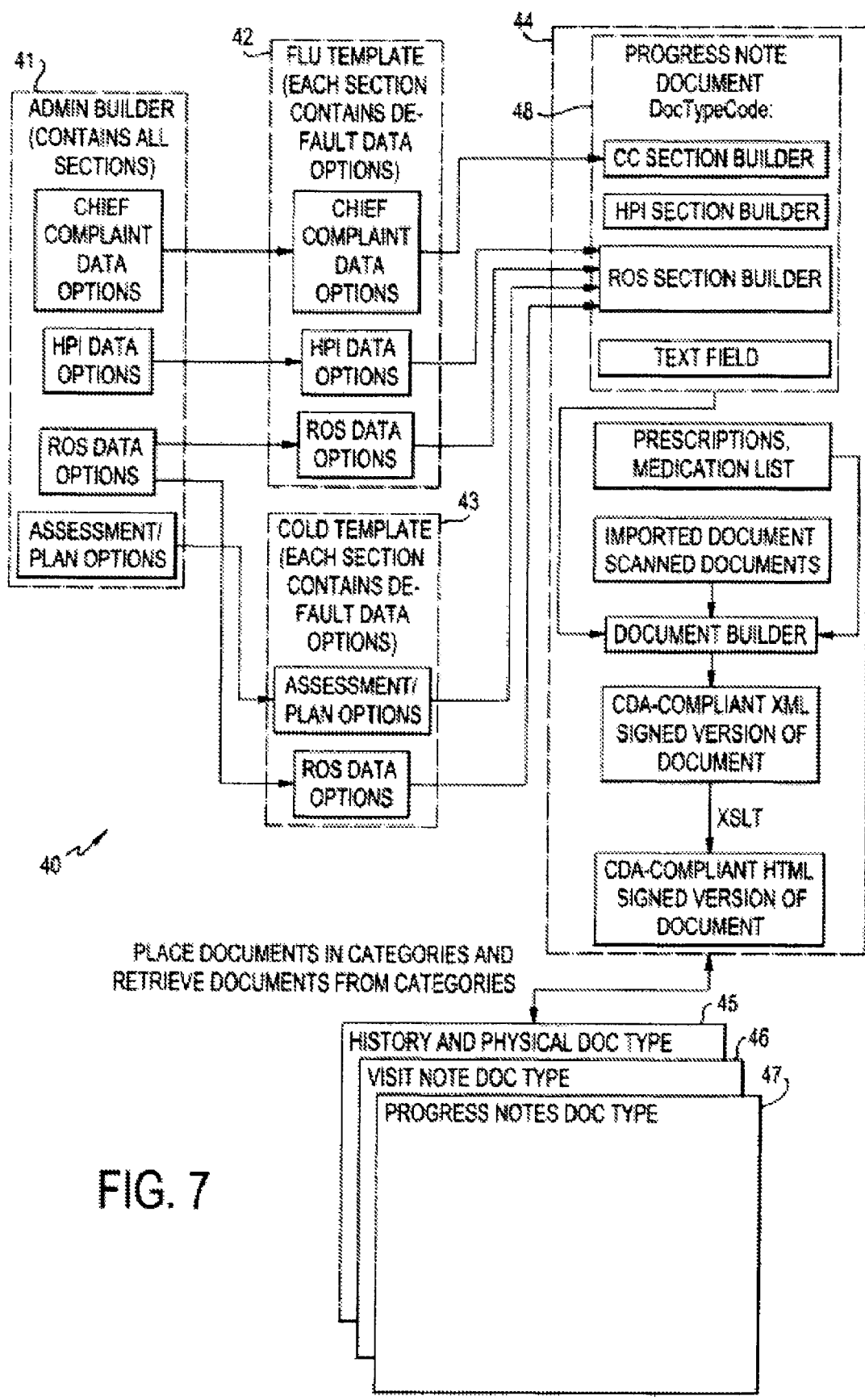
FIG. 7 is a block diagram of the clinical module 40 of FIG. 5.

If the user selects the chart option on the menu bar, the pull-down menu offers the user the option of accessing patient charts, build templates, or administration of HPI, diagnosis plan, family medical history, genetic screening, past medical history, past surgical history, physical examination, ROS, social history and general template administration. The chart option is supported by the clinical module 40 (FIG. 7).

The registration menu bar option allows the user to access patient information, visit information and delivery information, and is supported by the registration component 22 of the services server framework 20. The schedule menu bar option allows the user to access appointment scheduling and schedule information, and is supported by the scheduling module 23 of the framework 20. The system menu bar option allows the user to access report selection, security information such as group and user administration, and group rights, and system setup information such as care providers, communications, employers, locations, system configuration, system defaults and visit types. The system option is supported by the report, communication and system administration components 22 of the framework 20.

The envelope icon at the top right of the desktop gives the user access to the messaging center. If the icon shows a piece of mail (as in the embodiment of FIG. 10), the user has a new message. Clicking on the icon brings the user to the message center. A key icon is located next to the messaging icon, and allows the user to change the user password. The name of the user that is logged in is displayed to the right of the key icon, which is Kathy in the present example. Clicking on the user's name allows the user to log out.

A title bar is displayed beneath the menu bar. The title bar includes a flag icon, an information function and a search function. The present day and date are displayed on the right-hand side of the title bar. If the user clicks on the information button, a screen is displayed with information about the patient, including demographics, administrative and financial data which is retrieved from the registration and administration components 22 of the framework module 20. If the user updates any of the patient information, the updated information is updated at the registration component 22. The search button allows the user to search for a patient, by name, ID number, or other patient information.

If the user has selected a patient, so that the patient is in the buffer, the flag icon is activated in the title bar. The flag icon is an indicator of whether the currently selected patient has any flags checked in the patient flags modal. If the flag is clicked, the patient flags modal is displayed, which indicates whether the patient has been flagged for special attention.

Fields listed in the patient flags modal include: In Collections, No Insurance, Wheelchair, Violent, Excess Balance, Expired Insurance, Canceled Appointments, Missed Appointments, Collection 1, Collection 2, Collection 3, Sensitive Chart, Do Not Call Home, Do Not Release Name, Do Not Mail to Home, Medicare Waiver Signature, Restricted Chart, See Notes. The user can select to add or remove flags for a patient, and the system can automatically create a flag, such as when the patient has an outstanding balance on their account.

In the embodiment of FIG. 10, the user has configured the desktop to include a message from the messaging center, a listing of scheduled patients appointments and checked-in patients. The user is creating a message regarding medication refills. Once the user selects the patient name, the message is automatically pre-populated with information about the patient which is retrieved from the registration component 22 of the framework module 20. The message can also be pre-populated with the patient's chief complaint, and current medication information.

The listing of scheduled patients appointments can be configured by the user, but generally includes the time of the appointment, the patient name, any scheduled resources, the type of appointment, and the chief complaint. If the user wants to access patient information, the user selects a patient, which results in the patient name being displayed at the top right-hand side of the title bar, which is Laura Barrows in our example. The check mark to the right of the selected patient is a pull-down menu that displays a list of recently-selected patients. If the user selects a patient from that list, that newly selected patient will be the current patient in the buffer. The user can also select patients by selecting the search function from the title bar to search for the patient's name.

The system defines different types of users, such as clinical, research and administrative, each having different user rights. The desktop only displays those functions and information that are available for that particular user. For instance, the desktop would guide a clinical user into the EMR portion of the system, and the administrative user into the AR practice management portion of the system.

AR Module 30

Returning to FIG. 6, the AR module 30 is shown in further detail, and is implemented in accordance with the architecture shown in FIG. 3. The AR module 30 supports AR administration for a practice office. The AR module 30 summarizes patients' financial, medical and insurance information to produce a financial record of the patient's visit used in collecting payment for the services rendered.

The AR module 30 includes AR administration 31, procedure/financial mapping 34, service detail entry 35, insurance claims 36, claim detail/service detail history 37 and service details 38. The AR administration component 31 supports administration of the office practice, and communicates with the registration component 22, namely the patient information 32 and visit information 33. For instance, the AR administration component 31 includes look-up tables and configuration information, fee schedules, contracts and insurance companies and plans. The information in the AR administration component 31 is preferably set up by the practice office administration to be specific to the practice.

The patient information sub-section 32 supports patient information, including access, retrieval and storing. If a user wishes to access patient information, the patient information component 32 communicates with the registration component 22 of the framework module 20, which either stores the information or retrieves the information from a database. The patient information component 32 also retrieves insurance information from the AR administration component 31.

The information retrieved from the registration component 22 and the AR administration component 31 is presented to the user for display and manipulation. For instance, the patient information component 32 may pre-populate a form being viewed by the user, such as an insurance form or progress note, with the patient demographics and/or insurance information. Information that is new or updated from the patient is added to the customer workstation 12 and sent to the registration component 22 and the scheduling module 23.

The procedure/financial mapping component 34 supports billing codes from the reference database 26, such as Unicor/Alpha II and CodeCorrect, as well as charges, cost and time which are obtained from the AR administration component 31. The mapping component 34 relates procedures to the reason they were performed (diagnosis) and the charges, cost and time for those procedures.

The service detail entry component 35 retrieves information from the visit information component 33. That information is then used to pre-populate the associated date of service, providers, locations, and insurance plans for the service detail being entered. Information for the service detail component 35 is entered either manually from an electronic charge ticket or from a paper superbill, or can be entered electronically, such as by being electronically imported from the clinical module 40. The paper superbill is essentially a charge ticket that is used during checkout and/or billing and is created in response to the clinician's diagnosis and orders. The electronic charge ticket is an electronic representation of the paper superbill which may be used during checkout and/or billing either manually or through an automatic import.

The service detail entry component 35 sends information to the Unicor/Alpha II reference database 26 for validation prior to claim creation. Information from the service detail entry component 35 is used to generate an insurance claim. The information is sorted and stored in a database according to insurance claims 36, the claim detail/service detail history 37 and/or the service details 38. The service detail entry component 35 communicates with the clearinghouse 28 to process insurance claims, which responds to insurance claim requests with a pass, fail or error.

Figure 12:
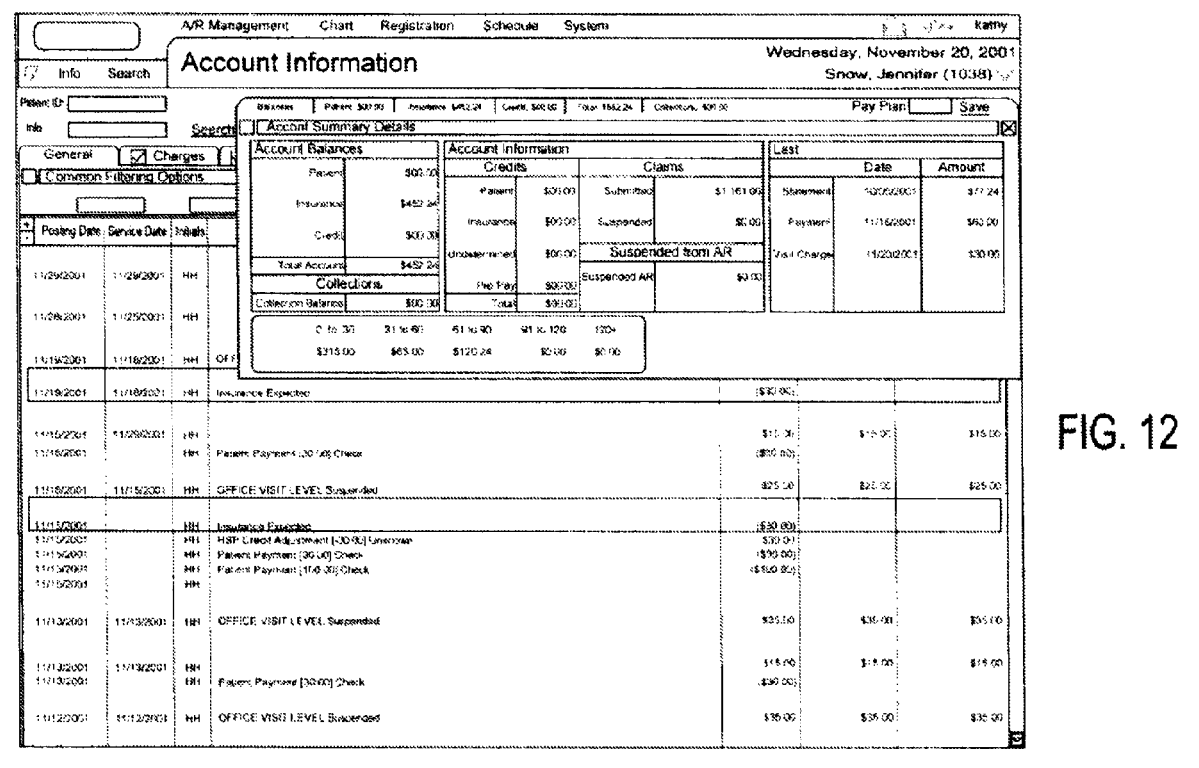

FIG. 12 shows account information for a patient. As the documentation for a patient visit is completed and authorized, all of the appropriate billing codes may be automatically posted to the charge entry portion of the system. Coding assistance is available for ICD, CPT, and HCPCS codes, and warnings and alerts are based on the Medicare reimbursement guidelines to facilitate coding and billing compliance.

The system then references the respective insurance plans, contracts and/or fee schedules to locate and enter the appropriate charges into the bill. Upon entry of the appropriate charges, a claim is generated and available for automatic electronic transmission. As payments are received, the system allows users to post payments and immediately reconcile the payments to ensure that all accounts balance properly.

Figure 13:
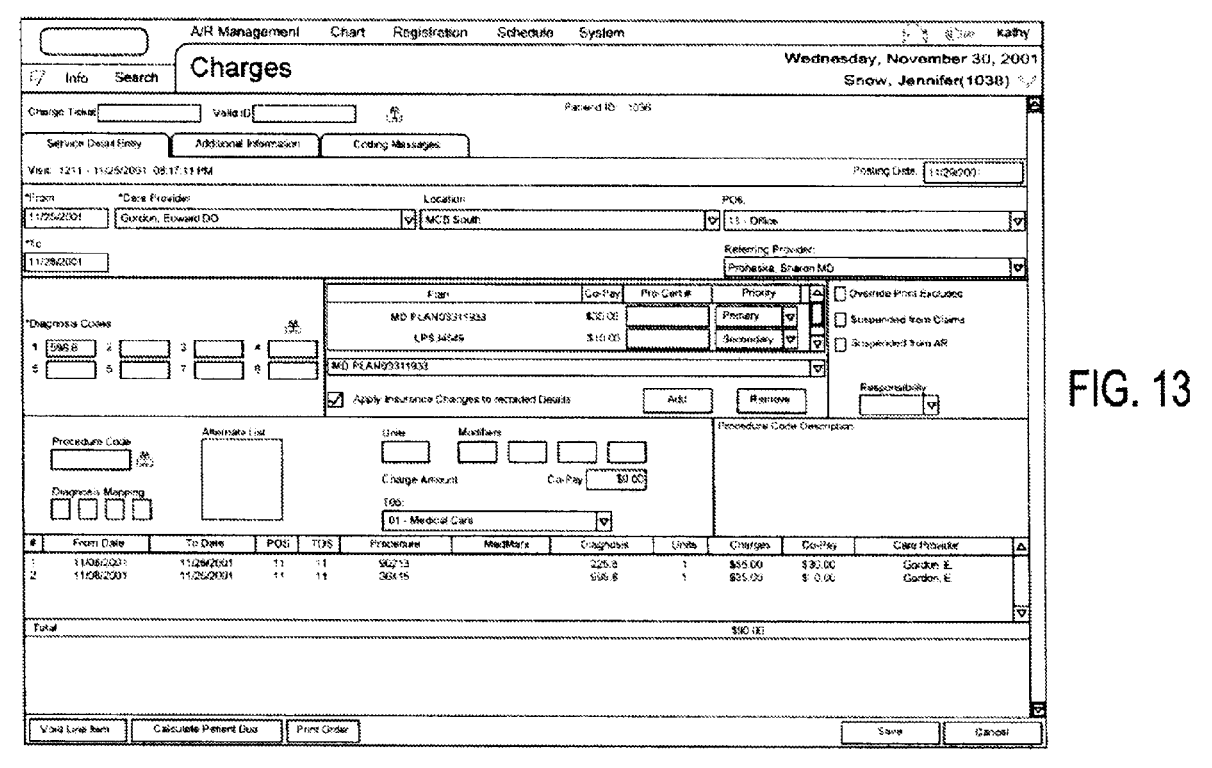

A sample of the charge posting is shown in FIG. 13. Charge posting consolidates and prepares the coding data as it comes over from the visit documentation captured within the system. Integrated coding edits enable the system to assist users in compliance with CMS and the National Correct Coding Initiative. Warnings and alerts based on the CMS reimbursement guidelines are displayed prior to saving the information, and available for reference purposes.

Additionally, users can search for all applicable diagnosis and procedure codes and arrange the format of a customized electronic superbill specific to the needs of the practice. When necessary, assignment of insurance coverage at the individual charge level is supported for tracking of charges within a single visit that are attached to different insurance coverage. Support for tracking multiple pre-certification numbers by insurance plan is included, and all patient demographic and insurance information is accessible for real-time edits during charge entry.

AR administration 31 also includes system parameters that allow accounting and claims information to be processed in "real-time" for automatic account posting and accurate reporting, or in "batch mode" for review and editing purposes. Users can also set up the administrative portion of the system to properly manage billing for multiple locations using a single Tax I.D.

Attachment of non-billable care providers to billable care providers allows more accurate revenue tracking. Users may establish multiple charges and descriptions for single CPT or HCPCS codes with defaults to streamline charge posting. Plan specific edits may be established to automate conversions of data for specific claim generation requirements, such as type of service or modifiers.

Claims and statements may consist of single or multiple pages and are automatically generated and available for electronic processing. Each claim that is created contains data for only one patient and for only one visit. After charges are grouped together by patient and by visit, they are then evaluated for multi-claim or multi-page separation. Once the claims have been created, they can be selected and edited prior to electronic submission. The system supports multiple claim formats including HCFA 1500, UB92 and ANSI X12N 837 and NSF. Claim payments are automatically posted and underpayment situations identified.

Claims management provides detailed filtering and sorting options that allow users to work with claims by insurance plan, date created, date submitted, claim priority, claim payment status, etc. This functionality provides quick access to claims information, notes and actions, as well as allowing users to view a claim in HCFA 1500 format.

Payment and adjustment posting retrieves the allowed amounts and contractual adjustments from the appropriate fee schedule and posts them simultaneously during payment entry. Additionally, applicable contractual adjustments may be posted at the time of charge posting, or during payment entry according to the respective insurance plan setup. Should insurance coverage change, the respective allowed amounts are automatically recalculated. Credit management allows users to select a credit category for designation of payment overages or credits. The utilization of these "credit buckets" reduces the efforts required for refund processing and balance transfers by reducing the research needed for processing credit balances.

Account information is quickly accessible for viewing, processing and editing purposes in summary and expanded line item displays. From the account line item view, all related transactions and notes can be displayed. Account information can be viewed in chronological order by date of service, posting date or visit order. Additionally, robust filtering and sorting options are available and can be saved for repeated usage based on job function needs.

The system also generates collections letters, and performs tracking of aged delinquent accounts and call tracking. Criteria can be defined so that accounts and claims qualify for concentrated collection and follow up activity by the office staff. Monitoring tools enable management to track and evaluate collection efforts.

Figure 14:
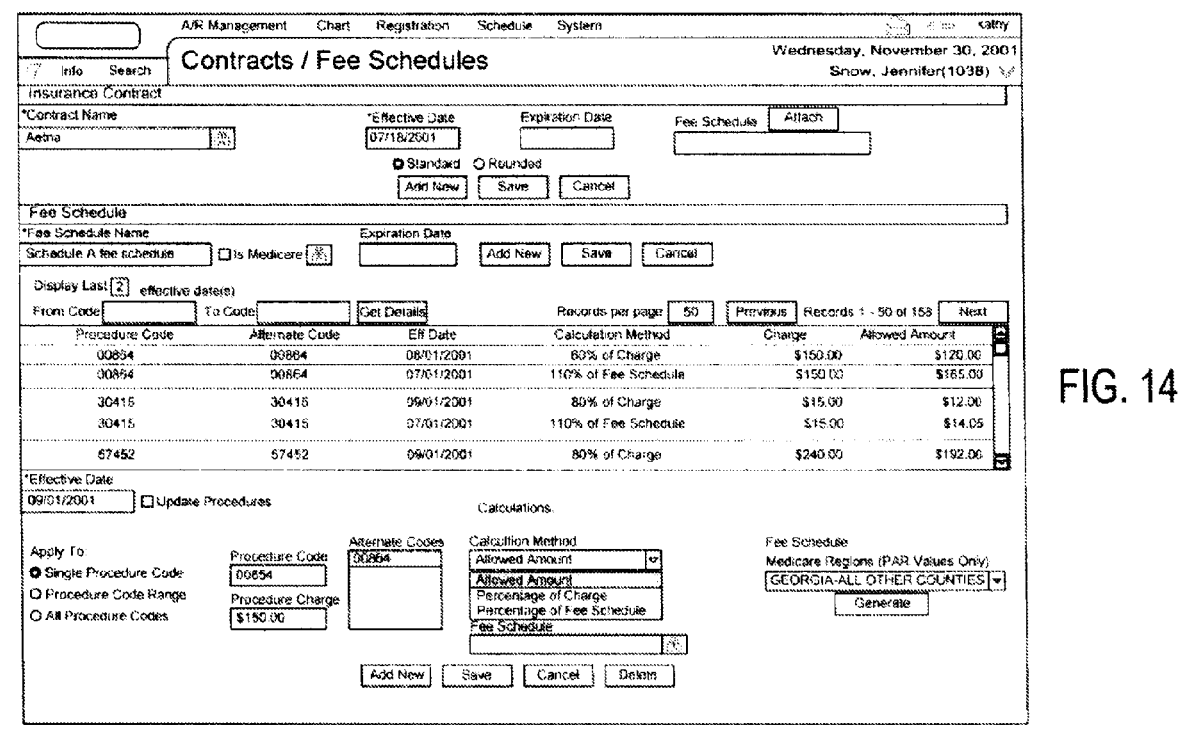

In addition, contracts and fee schedules can be set up and maintained with minimal effort, as shown in FIG. 14. Medicare part B fee schedules come pre-loaded with the system and are annually updated, enabling users to simply select the geographic region for their practice. The claim amounts are matched to the allowable amount of the contract to automatically establish the correct allowed amounts for procedures. A/R management gives users several methods to establish a variety of fee schedules: percentage of charge, allowed amount, percentage of another fee schedule (including Medicare), etc., and to indicate which of these fee schedules should be rounded and/or capitated. Contract fee schedules are integrated into the system's charge posting and payment entry functions.

Clinical Module 40

FIG. 7 shows the details of the clinical module 40, which has a template administration builder 41, templates 42, 43, document builder 44 and virtual file folders 45, 46, 47. The clinical module 40 supports the clinician's routines, from when the patient arrives at the practice office, until the patient leaves. The clinical module 40 is implemented in accordance with the architecture shown in FIG. 4.

Figure 15:
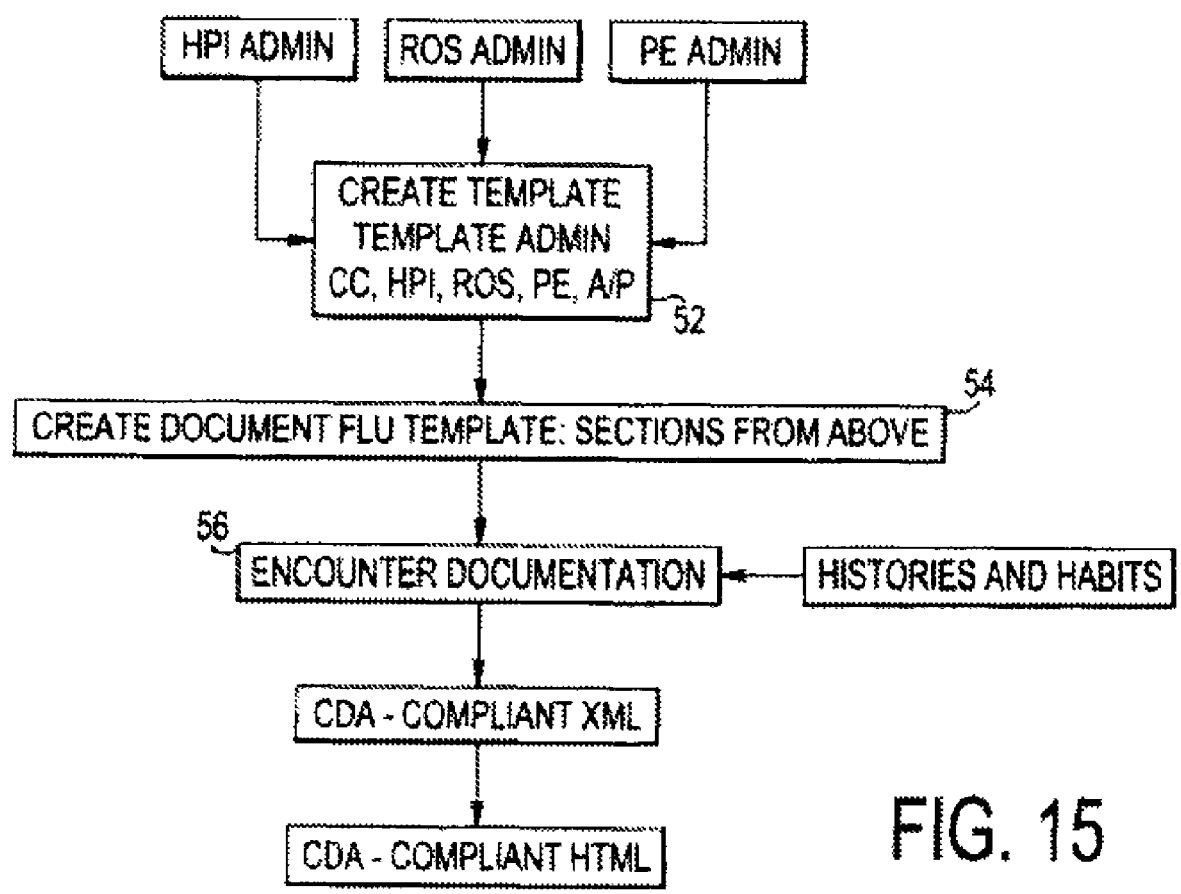
FIG. 15 is a flow chart depicting the overall operation of the clinical module 40.

The general operation of the clinical module 40 is shown in FIG. 15. The template administration builder 41 is used to create templates 42, 43 which are subsequently used to generate a document. Accordingly, at step 52, the user defines a template using one of the available template administrations, such as HPI administration, ROS administration or PE administration are first, then templates. Once the template 42, 43 is defined at step 52, it can be used to create documents by the document builder 44, step 54.

At step 54, the template builder 48 gathers information which, together with prescription and medication lists and any imported documents, is used to build a document, step 56. The template builder can gather information from the registration component 22, such as CC and/or demographics, or information about history and habits that may have been entered during triage or documentation of prior visits. The template structure ensures that a document can convert between XML and HTML formats. The document is sorted and stored in a file system 45, 46, 47, in accordance with its document type.

The clinical module 40 supports the use of a triage note which prompts the clinician to enter in detailed triage data for a patient. It is designed to be the initial documentation point in a patient's visit and will usually be completed by a nurse before the patient starts the encounter with the clinician. All information entered in the triage will be used in other sections of the patient's visit as well as their patient record. The information available for entry includes Reason for Visit, Presenting Symptoms, Additional Notes, Vital Signs (Blood Pressure, Heart Rate, Respiratory Rate, Temperature, etc.), Review of Systems and Orthostatic Vital Signs. The Reason for Visit is updated in the visit check-in information of the registration component 22 of the framework module 20, for use by other areas of the system.

Figure 11:
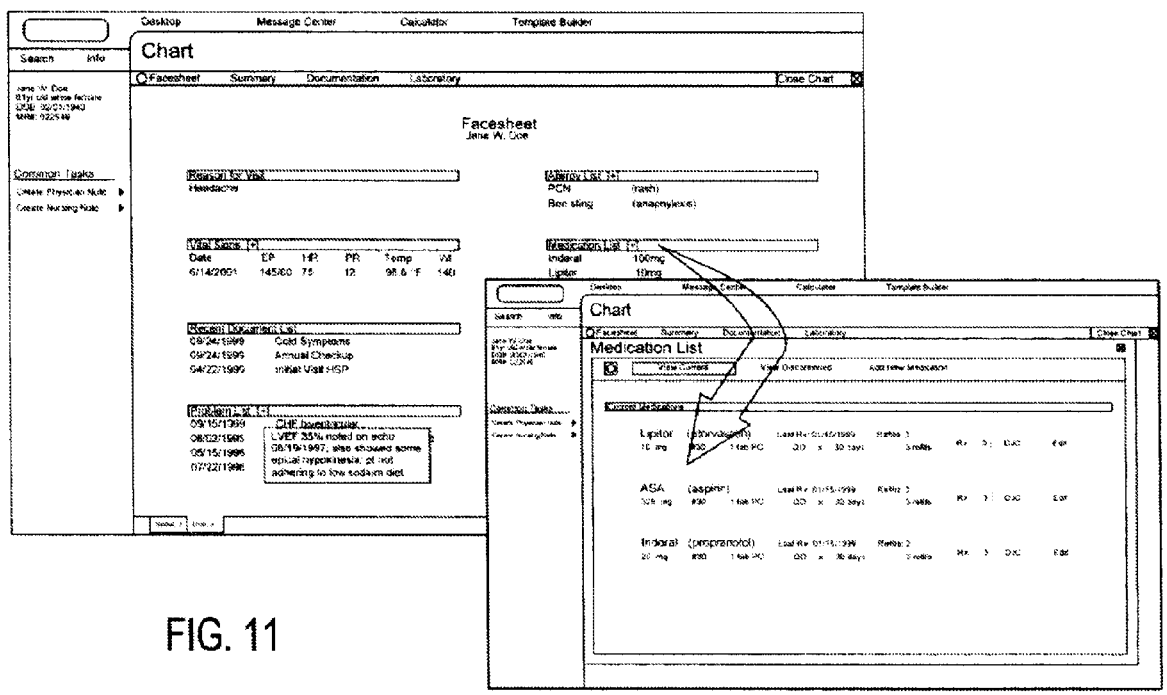
FIG. 11 shows the facesheet screen of the clinical chart module 40 of FIG. 7.

The clinical module 40 supports the patient charts, or EMR. If the user selects Patient Charts from the Chart option of the Desktop menu bar (FIG. 10), the facesheet is displayed, as shown in FIG. 11. The facesheet of the currently selected patient chart is displayed when a user opens a patient chart. It contains critical but brief patient information most frequently used by the physician and nurse. It serves as a "homebase" allowing quick and easy access to more detailed parts of the chart. It allows the user to view and add vital clinical information (Vital Signs, problems, medications, Allergies etc.) at a glance without having to navigate further into a patient's chart.

As shown, the facesheet preferably includes the patient's reason for visit, vital signs, problem list, past medical history, medication list, and other pertinent information regarding the patient's medical history, which may have been entered during registration, scheduling or triage of the patient, or from a prior patient visit. The information displayed within the facesheet can be customized to show different information lists. In FIG. 11, the clinician has chosen to add a new medication to the patient's medical record. Also, the clinician has multiple patient records open, as shown by the multiple tab options listed across the bottom of the screen. The clinician can simultaneously see and rotate amongst multiple patients while also having immediate access to each patient's specific information.

The patient chart also allows the user to view summary information (a summary report), which includes, for instance, a listing of allergies, medications, family history, genetic screening, past medical history, past surgical history and any other user-defined information. The Documentation selection of the patient chart presents the user with a listing of all of the patient documents, such as Progress Notes, H&P Notes, Triage Notes and scanned documents. The documents can be amended, printed and cosigned.

The user can also move to any other area of the system from the patient charts section, and can create a document, such as an H&P Note, Miscellaneous Note or Progress Note or Nursing Notes such as a Triage Note or Miscellaneous Note.

The clinical module 40 and the Desktop 22 support the following operations: indicating to the clinician that the patient encounter has begun by indicating that the patient has arrived and to retrieve the patient from the waiting room; entering the patient's height, weight and vital signs; review and update or record the chief complaint, allergies, current medications, past medical, family and/or social history, present illness, review of symptoms, miscellaneous notes; allows the clinician to review previously entered information, including demographics and progress notes; update any patient information in the system; record the results of a physical examination, the clinician's assessment; automatically code the diagnosis (based on selections that were made during system setup and template building); record the clinician's plan; generate and document prescriptions and orders; record treatment; select evaluation and management codes; generate a superbill for checkout processing; and close the patient encounter.

The clinical module 40 forms the Electronic Medical Record (EMR), which is comprised of all documents generated by the user for a patient, including facesheets (FIG. 11), Progress Notes (FIGS. 37-38) and H&P Notes (FIG. 40). The EMR provides an automated encounter documentation process and electronic patient record solution within an easy to use interface that is both mobile and secure. Clinicians can electronically access and update all of their patient' records within the practice while seeing patients, and have remote access to patient records to assist clinicians while "on-call" or at the hospital.

Patient data can be entered in different formats, including scanned documents, dictation, transcribed electronic documents and through interface with third-party software and devices which capture results. The data is stored in the patient's electronic record. The EMR eliminates redundant and illegible data in patient records, and focuses on quick, dynamic generation of accurate notes that adheres to regulatory guidelines.

Authorized users may access the same patient record simultaneously to review patient medical history and vital signs, capture a patient's history of present illness, review of systems and physical exam, document an assessment and plan and have orders and prescriptions automatically generated for fulfillment by labs or pharmacies. Patient information can be displayed in multiple views and formats, such as text, form, table, flow sheet, or graphs, to facilitate rapid chart review and determination of the context in which a patient's symptoms occur.

As the clinician completes the encounter documentation, the appropriate ICD, CPT and E&M codes are suggested and captured for automated billing purposes. Thus, the EMR automates the entry of charges into the A/R Management portion of the system for proper billing and claims filing, thereby reducing lost charges, ensuring that third-party reimbursement requirements are met, and increasing revenue. The coding and billing process is initiated and any patient documentation is electronically signed.

Thus, the system eliminates the need for separate E&M coding for office visits through the automatic calculation and suggestion of the E&M coding level based upon template-driven point-of-care documentation. The system includes an integrated coding database which facilitates proper documentation and improves reimbursement by enabling compliance with government and insurance coding guidelines.

The patient record is the medical record for a single patient. Each patient's medical record contains instances of documents. The document instance is a single entry in a patient's record. Each document instance added to a patient's record has a date/time stamp and may be associated with a visit. It also has a document type associated with it, for example a Progress Note, or a Triage Note, or a History & Physical. The document type is used to sort and filter documents when viewing the list of documents in a patient's record.

Template Administration

Template administration permits the user to conduct administration tasks for various document sections, such as ROS, PE, and HPI. The main function of template administration is to create configured or customized templates, step

52 of FIG. 15. Templates are configurable by the user, either by creating a template from scratch or by editing a standard or existing template.

An example of building a template is shown in FIGS. 16-32. At FIG. 16, a template administration screen is shown which permits the user to create, edit, or delete templates. The templates are organized in folders and displayed in a table. The user may add, rename, or remove folders and move files between folders.

The administration builder 41 is used to establish documentation choices for the chief complaint, HPI (history of present illness), ROS (review of symptoms), PE (physical examination) and assessment/plan. The administration builder component 41 is used to prepare templates 42, 43 which assist the clinician in entering data into the system, which in turn are used to generate progress notes that are retained in the patient's EMR. The templates are used to guide the user in building a document, as reflected by the unidirectional arrows from the data options of each of the templates should into the corresponding sections of the template document builder 48.

Figure 16:
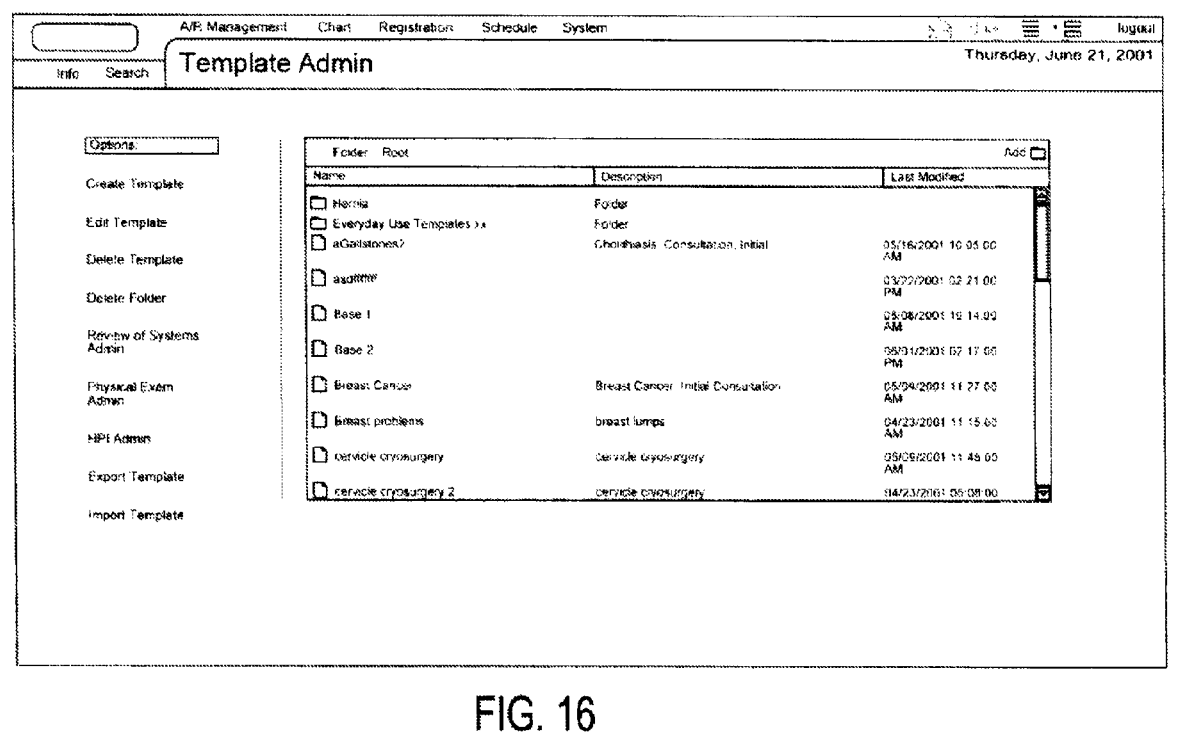

To build a custom template from scratch, the user selects to create the template from the options displayed in FIG. 16, and identifies the type of template to be built. If the user selects to create a procedure note template, for instance, the system would exclude data categories for ROS and PE since those categories are not applicable to a procedure note.

Figure 17:
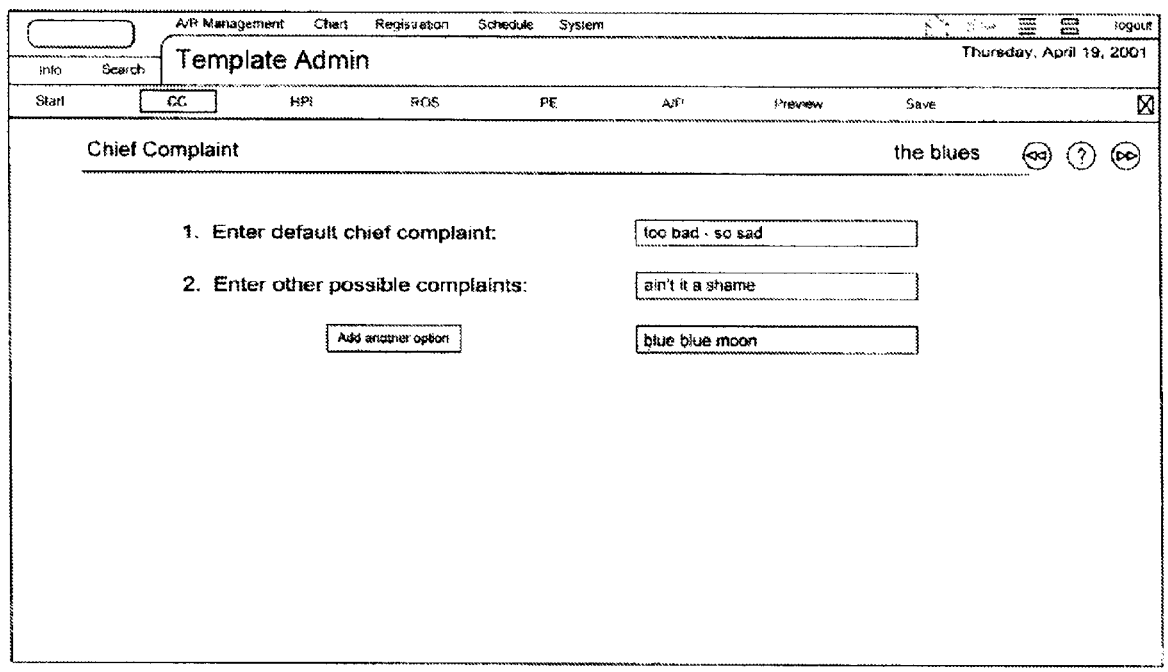

Once the type of template is selected, the system guides the user through the process for creating the template. The system defines the appropriate sections for the template, such as Chief Complaint, HPI, ROS, PE and AP (assessment and plan). FIG. 17 shows the initial section to be defined by the user, Chief Complaint. The Chief Complaint is a concise statement describing the patient's symptom, problem condition, diagnosis, physician recommended return or other factor that is the reason for the encounter. This field includes the chief complaints identified by the user to include in the template. The system allows the user to define a default chief complaint and other possible complaints. The user can add additional chief complaints by clicking the "Add another option" button or tabbing out of the textbox.

Figures 18, 19:
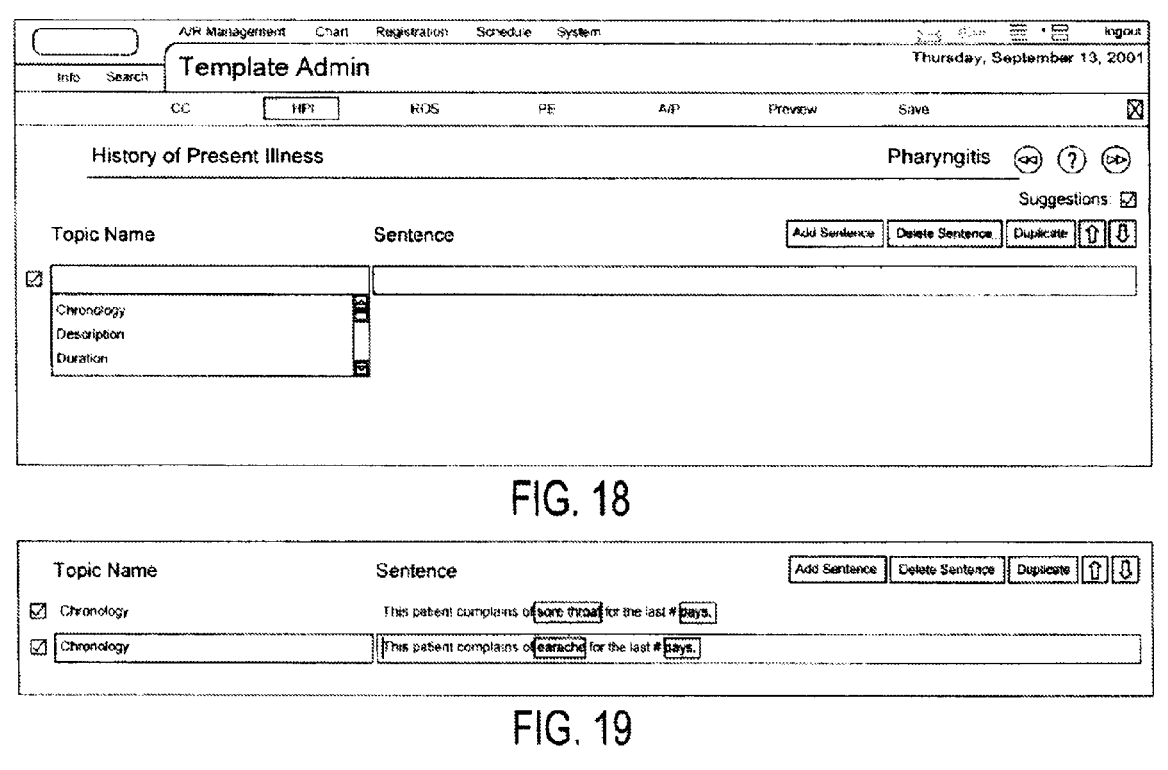

Once the user completes the CC section, the navigation button brings the user to the History of Present Illness section template builder, as shown in FIG. 18. The History of Present Illness is a chronological description of the development of the patient's present illness from the first sign and/or symptoms or from the previous encounter to the present. It includes the following HCFA recommended elements: Location, Quality, Severity, Duration, Timing, Context, Modifying factors, and Associated signs and symptoms.

The History of Present Illness template section builder is used to add topics and the related text to include within a template. Subjective information routinely reviewed with the patient for a particular complaint or disease process should be included. Such topics may include one of the HCFA recommended element names (including chronology, onset, description, intensity, exacerbation, etc.) or one of the user's own choosing. Related text can then be typed in the sentence as one might normally report the finding.

Within the sentence, text may be selected, options such as text entry fields or drop-down boxes can be specified, and appropriate responses included. Other text options include patient specific demographic information or gender specific pronouns to default into the sentence. The HPI template section builder is used to define the elements of the History of Present Illness that may need to be addressed when a patient presents with a specific complaint or group of complaints. The HPI selections will be unique to the template it is created within.

As shown in FIG. 18, the template builder provides a drop-down menu for the topic name field. The user can select from the defined list or type a topic name that will display within the template builder and describe the information that the related sentence addresses. HCFA recommended elements are denoted by a different color. Specific sentences are associated with each topic name. As shown in FIG. 19, if the user selects the topic name Chronology, the sentence "The patient complains of _____ for the last _____ of _____." The suggested sentences are pulled in from the HPI administration piece.

The user can attach control types to text within the sentence by highlighting or selecting a phrase, as shown in FIG. 19. A list of available control types is displayed for selection by the user. Control types include, for instance, Care Provider List, Date Stamp, Duration, Measurement, Make Input Box, Make Multiple Select, Make Select List, Number Selector and Demographic Information. The Care Provider List attaches a list of care providers; Measurement is used to select a number and unit of measure; Make Input Box enables the user to create a point in the sentence where data can be typed; Make Multiple Select allows the user to identify and add a list of multiple choices that will be available in the sentence when using the template.

The Make Select List option creates a list of options that can be applied to a selected text within the sentence. The user can branch the sentence to give more details about the sentence contents. For example, if the patient responds positively to the question "Have you ever had these symptoms before?" then the physician may follow up with questions such as "How long ago?" and "What treatments were used?" If the patient responds negatively to the initial question, the physician does not need to ask the follow-up questions. The Demographic Information control type attaches the text "age/race/sex" control to this point in the sentence. When the template is being used in the document builder, the patient's age, race and sex will populate the field.

Other control types include He/She, Him/Her, Himself/Herself, and His/Her. These control types are used to designate a point where the correct gender specific pronouns will default into the sentence.

Figure 20:
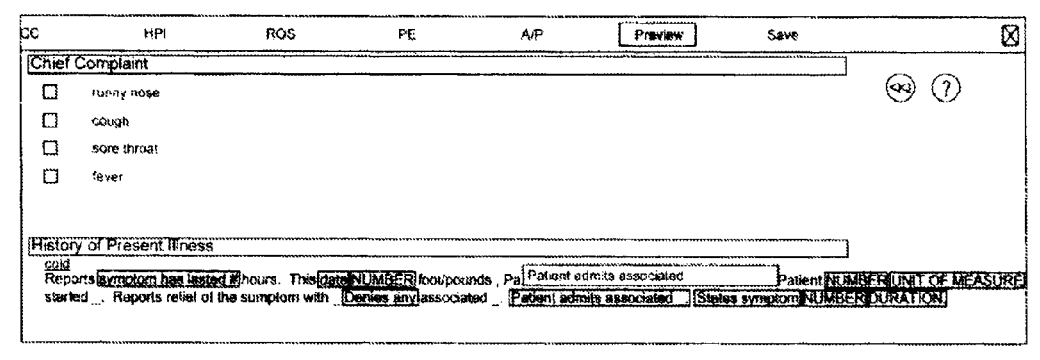

The user can preview the selected choices, as they will be viewed in the template, at any time during the building process. All body systems and associated elements of exam may be available to all templates. A preview of the template is shown in FIG. 20, for both the Chief Complaint and History of Present Illness sections.

Figure 21:
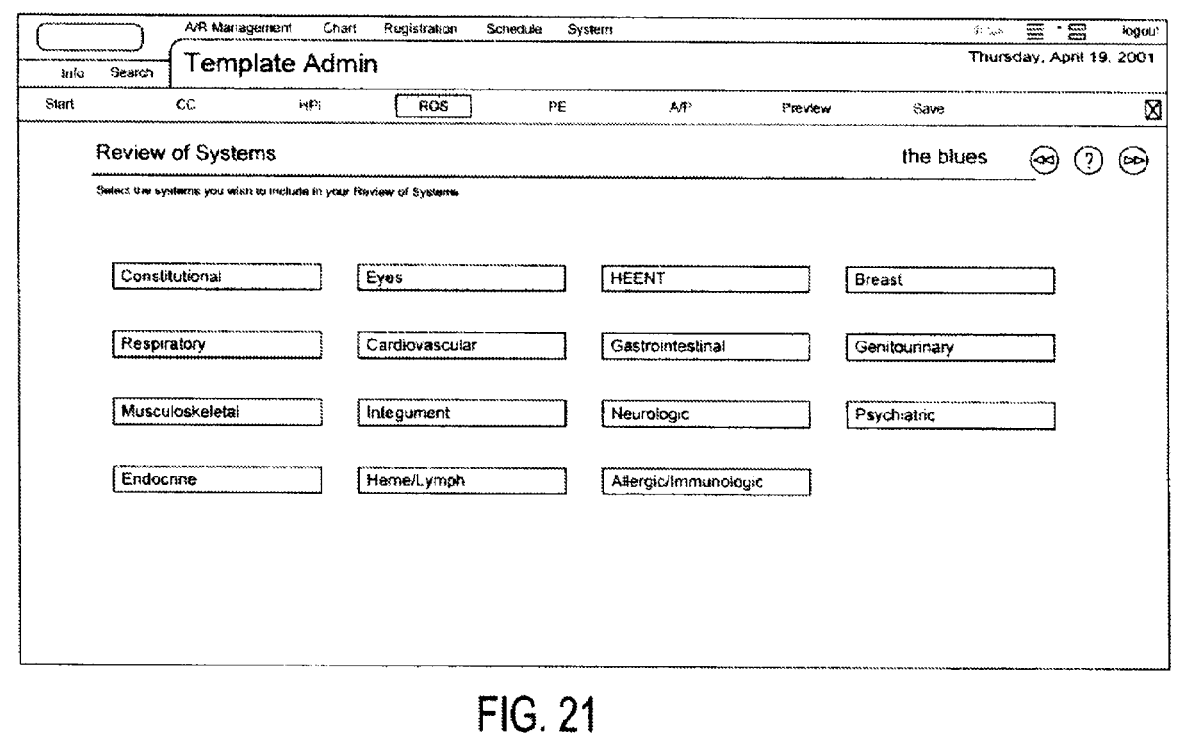

As shown in FIG. 21, the ROS template section builder displays a list of body systems the user can select to add to the template. Once the systems are selected, the user will navigate to the next page and select the items associated with the body system that are regularly reviewed with the patient. Users will ask the patient questions about the body systems, depending on the reason for visit.

For each of the body systems selected from the inventory, the examination element is displayed, as shown in FIG. 22. Comprehensive sets of elements and modifiers have been included as system defaults for each system to cover a general review of systems. Each user may build the elements into his templates according to practice needs. As each system heading is selected by the user, multiple symptoms related to that system are displayed. As shown in FIG. 22, the user can also define the default settings for the symptom to appear neutral, negative or positive. This allows the user to more quickly document the findings, eliminating clicks of the mouse (or taps with the stylus) during the encounter. The user can also define any modifiers that can be added to further detail the conditions.

The ROS administration section of the chart allows the user to specify which symptoms will display for each body system, and in which order. It will also allow the physician to set normal default text. The user may choose to add additional symptoms. The ROS administration must be used to perform additional actions that are not available from this page. Any symptoms added to the ROS administration page will be available to all templates and not just the current template being edited. The options selected during the ROS building display with the associated default responses for positives and pertinent negatives displayed.

Figure 23:
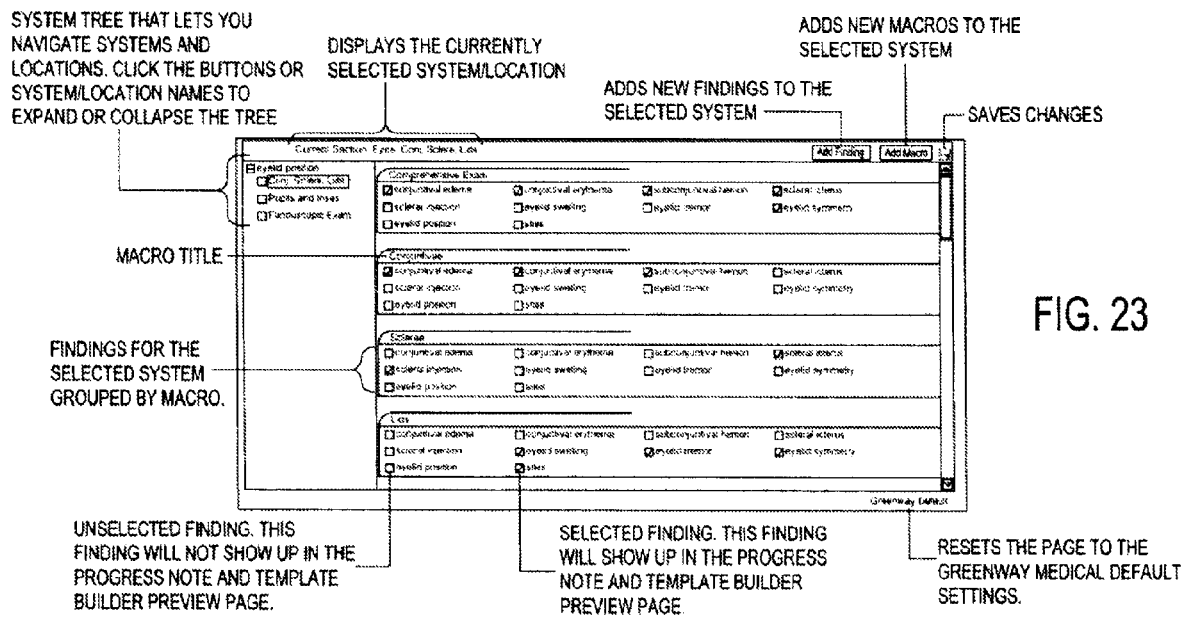

FIG. 23 shows the PE administration of the template builder. The setup chosen by the user is applied to all document templates having a PE section, such as Progress Notes, H&P Notes, etc. The PE administration can be accessed from the desktop or facesheet. The PE administration enables the user to configure a page that is used as a worksheet or checklist for the physician's physical examination of a patient.

Systems is a label for the systems that are displayed on the administration page and are also used as a guideline or checklist for the physician during examination of the patient. The categories are displayed in the following order by default (to correspond to the CMS default): Constitutional, Eyes, HENT, Neck, Chest, Cardiovascular, Breasts, Gastrointestinal, Genitourinary, Lymphatic, Musculoskeletal, Skin, Neurologic, and Psychiatric. Each category is a body system and is therefore a component of the physical exam. As each category is opened, there is a level of subcategories displayed beneath. Subcategories can be created to greater and greater levels on the page. The system will support as many levels as the user wishes to create.

The findings content area displays the various systems available to the user. In the example, the user has chosen Eyes, and that selection is displayed in the title or control bar. The system Eyes has four macros, namely Comprehensive Exam, Conjunctivae, Sclerae and Lids, which is also listed in tree format in the navigation sidebar. The user can use the navigation sidebar to move between the various systems and locations, and can expand and collapse the systems and macros in the tree.

One or more findings are listed for each macro that is displayed. The user can add new macros and/or findings to the selected system by using the control buttons in the control bar. The user is then presented with a list of the current macros or findings, and can add, delete, reorder or edit any of the macros and findings.

The user selects those findings that the user would like displayed in the progress note and template builder preview page. Unselected findings will not show up in the progress note and template builder preview page. Once the user selects a finding, the user is presented with a list of defined values for the specified finding. The values are listed in the order that they will be displayed in the template. The user can select one or more of the displayed values to be the default value for the finding, and can add, delete, reorder or edit any of the displayed values. The selected values will appear on the template when the user selects the finding during document building. The user can then select the values that are appropriate to be added to the document being built, or can add, delete or edit those values.

The user can also associate one or more modifiers to any of the findings. The modifiers are listed according to categories, such as measurements, locations, descriptions. An example of a modifier would be "inches" for the finding "eyelid symmetry", which would be displayed on the template and allow the user to specify a measurement in inches to be associated with that finding. The user can add, delete or edit the categories and modifiers.

The systems are linked to E/M coding by the system. Because of this, the findings of the physical exam which are selected from the default menu will all be linked to E/M coding. The user/caregiver may add his/her own findings, which will also be linked to the E/M coding by virtue of their being located in subcategories (folders) that are linked. The user may also link his added findings and subcategories to SNOMED CMV via the SNOMED selection tool, which is available on the page to allow the user to search the SNOMED database.

Figure 24:
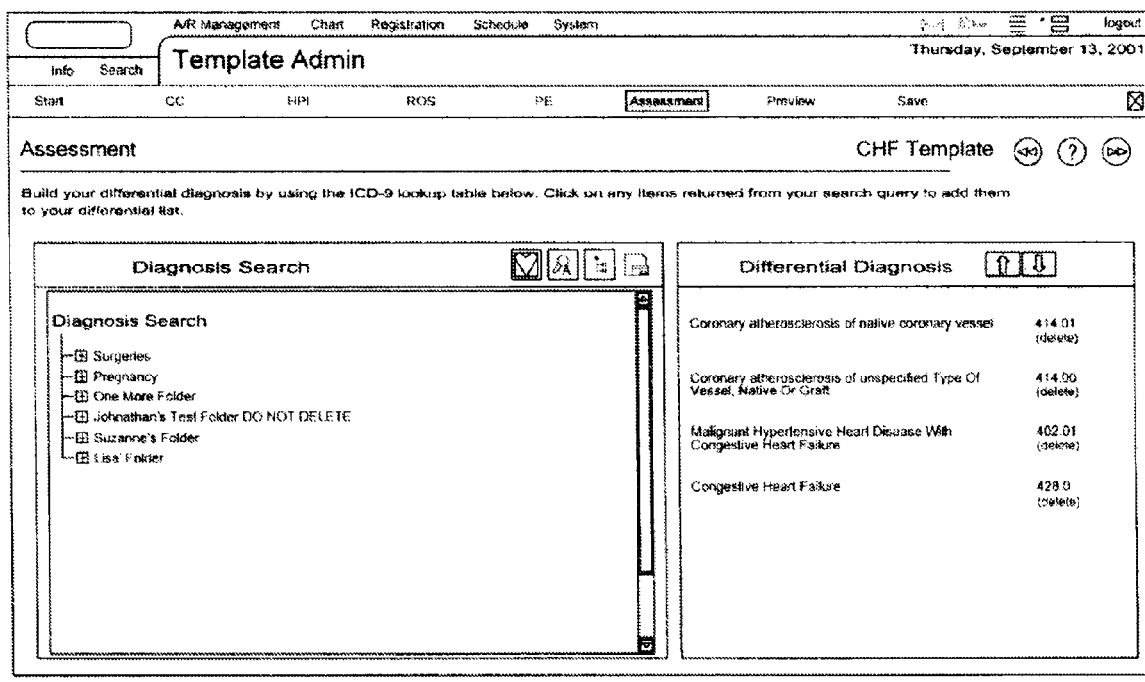
Figure 25:

The next section in the template builder is Assessment. As shown in FIGS. 24 and 25, the Assessment template builder section allows the user to build a differential diagnosis list for the present template. The user selects a diagnosis from a previously built "favorite" diagnosis list or searches for diagnoses using the ICD-9 search tools.

Figure 26:
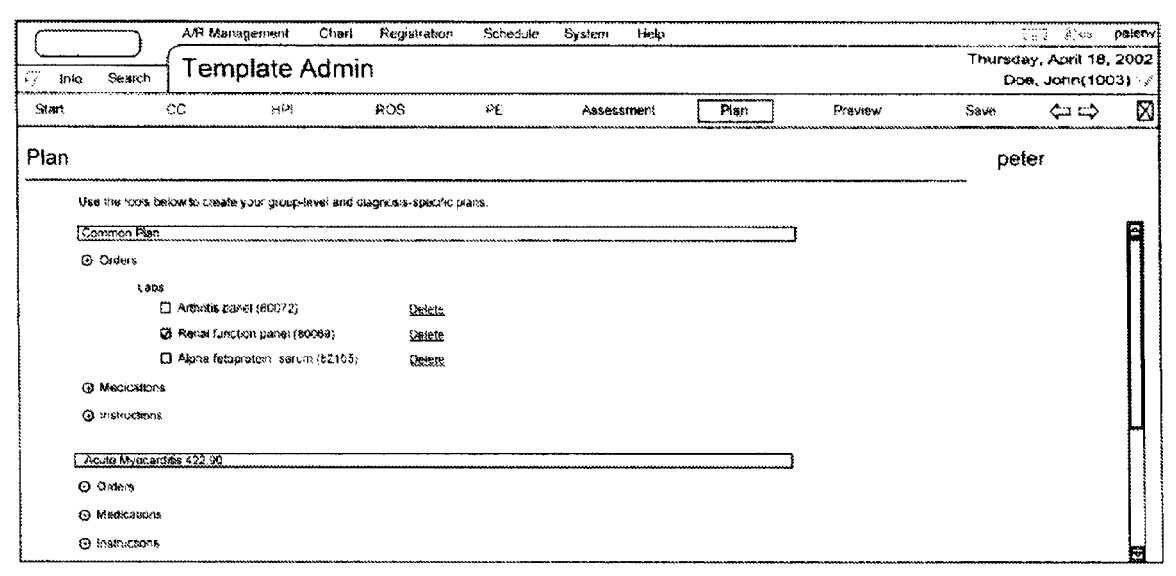

FIG. 26 shows the Plan section building administration, which is used to create group-level and diagnosis-specific plans. The Plan section building can be accessed from the Template administration page, and is part of creating a Progress Note or H&P template. The group-level plan, shown as the Common Plan, is used to define a plan for the template, whereas the diagnosis-specific plans can be created that are specific to a clinician's diagnosis as selected from the differential diagnosis list in the present template.

Figure 27:
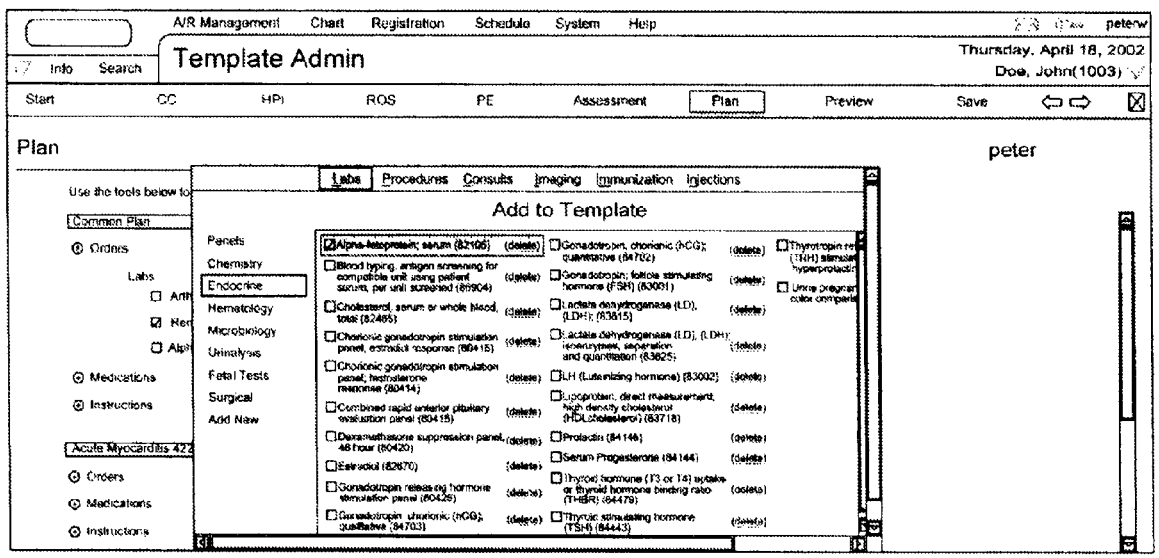

There are preferably at least three parts to each plan, namely Orders, Medications and Instructions. In FIG. 27, the user has selected to configure the Orders, and a menu list is displayed having various Plan Types and Categories. Plan Types include Labs, Procedures, Consults, Imaging, Immunization and Injections. In the example, the user has selected the Plan Type of Labs, and the Categories for Labs is displayed as Panels, Chemistry, Endocrine, Hematology, Microbiology, Urinalysis, Fetal Test, and Surgical. The user can create new Plan Types.

Once the Plan Type is selected, the user can choose from amongst the possible Categories, or can create a new Category. The user has selected the Category Endocrine, and the list of Labs for that Category are displayed for the user's selection. As shown in FIG. 26, the user has selected two Panels and an Endocrine from the menu list. The selections are displayed on the Plan page beneath Orders for the Lab Plan Type.

The user can preview the entire template that he/she has created, rather than in separate sections. In the preview mode, the user is able to view the template sections as they will appear when creating a document using this template. The user can see items in each template section and may add omitted items or delete unnecessary items.

Figure 28:
Figure 29:
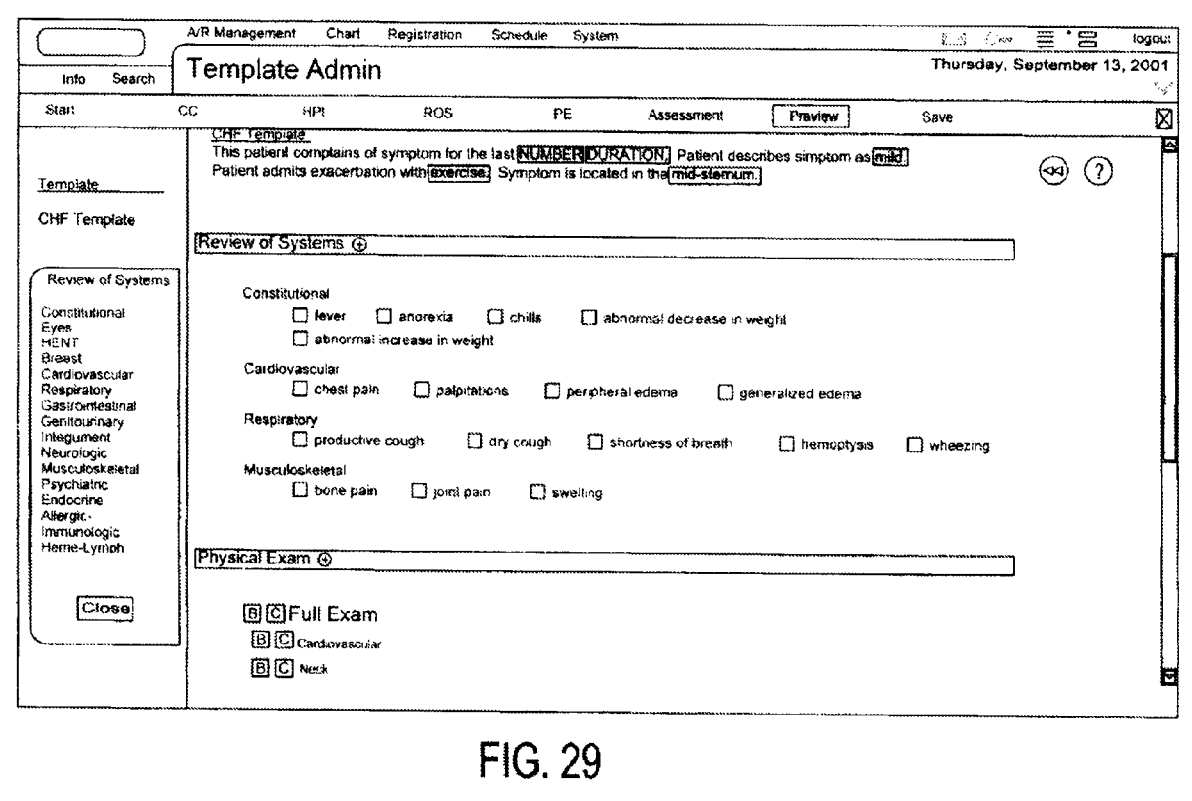

FIGS. 28 and 29 show an example of template preview. FIG. 28 shows the various sections of the template built by the user. At FIG. 29, the user clicks the "+" button beside the Review of Systems label and the ROS list is displayed in the action bar. The user may then add or delete systems in the ROS Template Section. However, in order to edit the symptoms within each system, the user must return to the ROS template builder section and/or the ROS Administration page.

Figure 32:
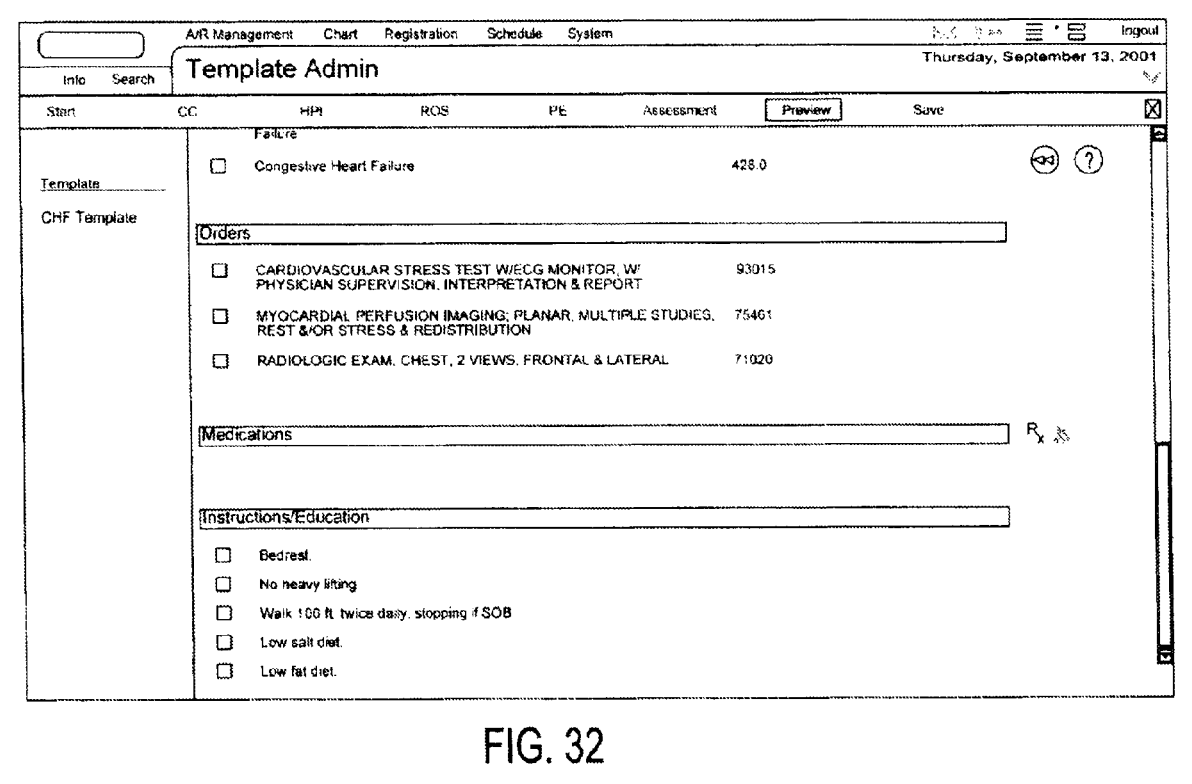

FIG. 30 shows the preview for the Physical Examination section. The use can either select the option "B" to preview a basic exam, or can select option "C" to preview a comprehensive exam. At FIG. 31, the user is previewing the Assessment section of the template. If the user selects a diagnosis from the Assessment (congestive heart failure in the example), the Orders, Medications and Instructions or Education pre-fill into template sections, as shown in FIG. 32. The Orders, Medications, Instructions and Education are associated with the selected diagnosis.

Document Builder 44

The document builder 44 supports the creation and generation of documents such as Progress Notes, which is implemented through the use of templates. A template is a pre-defined set of data options that is used to dynamically generate a document. Templates do not specify how sections are presented to the user, but rather the data that is utilized at the time of documentation. A document may be created using no template, one template, or more than one template. For instance, the Flu template and the Cold template can be combined for a new visit document where the patient presents with flu-like symptoms.

The document builder 44 includes features that assist the user in quickly building document text for each section of a document for the patient chart. Multiple data capture formats are supported in this feature. Data options defined in a template may be used to further simplify creation of that section of a document. For example, a "normal sore throat" template may have been defined to automatically populate the CC, HPI, ROS, PE, and A/P sections of the document with appropriate questions and answers for a patient presenting with a sore throat.

The system has intuitive templates 42, 43 with easy-to-use point and click data entry and optional keyboard use. There are multiple ways to enter information, from point-and-click using the templates, to drawing on the input device, taking digital photographs or video, dictation (voice recognition), audio, typing, and hand writing (handwriting recognition). Information can be viewed as text, in table form, as a flow sheet, or as a graph. The user has a library of templates to choose from, with certain templates being for general use by nearly all clinicians, and other templates beings detailed to specialty clinicians such as dermatologists and urologists. In addition, the user can create templates from scratch, or by editing other templates.

The templates 42, 43 facilitate the entry of information into the system in a manner that is easy to use, intuitive to the user and faster than making paper entries. The templates 42, 43 help the user ensure that all necessary information is entered so that documentation is complete and accurate. The system provides for direct entry of documentation into the computer, eliminating the need to dictate, review and sign transcription. The templates 42, 43 allow the user to pull forward data from prior visits, so that the clinician can simply note changes since the last visit without re-recording information that was previously collected and has not changed.

The system primarily has three types of templates: history and physical ("H&P")/progress notes, procedure notes, and consultation notes. Summary lists (such as medication, allergy and problem lists) are automatically updated directly from progress note documentation. The templates automate the generation of documents for consultation correspondence, hospital admission, H&P (history and physical) documentation, procedure notes, work and school excuses, and other standard communications.

In the exemplary embodiment of FIG. 7, a flu template 42 and cold template 43 are shown. Each H&P/Progress Note template may include the following sections: chief complaint (CC), history of personal illness (HPI), review of systems (ROS), physical examination (PE), Assessment and Plan. The flu template 42 includes sections for chief complaint, HPI and ROS, and the cold template 43 has assessment, plan and ROS sections, which are defined in the respective sections of the template builder component 41.

Each section of the templates 42, 43 permits the clinician to select from among a list of default data options. For instance, the ROS options available to the clinician for the flu template 42 may include runny nose, sinus drip, sneezing, and difficulty breathing. The template building and document building are designed to track the manner in which a clinician would typically record events at a patient encounter process on paper, from CC to HPI to ROS to PE to Assessment to Plan. However, the user can jump from one section to another and need not follow any particular order.

The templates are used to quickly generate documents. Once the clinician has completed the template 42, 43, the document builder 44 generates a progress note that will be retained as the final document for that patient encounter. The document will have a main body section that consists of the sections from the templates 42, 43, as well as a section for histories and habits to address patient history information such as past medical history, specific condition history (e.g., cardiac history), surgical history, medications, allergies, family medical history, genetic screening, social history and problems. In the example of FIG. 7, the main body section of the document being generated for flu template 42 indicates the chief complaint, HPI, ROS and any other text entered by the clinician.

The document builder compiles the various sections into a document based upon the clinical document architecture (CDA), as defined by HL-7 (Health Level 7, a standards body). The document can be electronically signed. The document is created in XML format, and can be converted into a modified XML format which is compliant with the HL-7 CDA standard by XSLT processing. Once the document is created, it is sorted according to its document type, and stored in a respective file system 45, 46, 47, where it resides in the patient chart. The documents may be sorted, for instance, by document type (e.g, History & Physical, Progress Note, Procedure Note, etc.), document status (e.g., Authenticated or In Progress), creation date/time, or by the user who created the document.

Document Building—Progress Notes

The Progress Note is an example of a document that is created by the document builder 44 in accordance with a pre-defined template. The Progress Note is the physician's primary note for a particular patient encounter, and is amendable and printable. The system extensively uses intuitive graphical user interface technologies and electronic drawing tools to ensure that an entire patient encounter can be documented by just pointing and clicking through the patient record. However, the system also allows for keyboard entry as an alternative method to input information. On average, a clinician can complete a Progress Note in about 1-2 minutes or less. Once the Progress Note is completed and electronically signed by the clinician, the note is saved and available for printing and future access.

Figure 33:
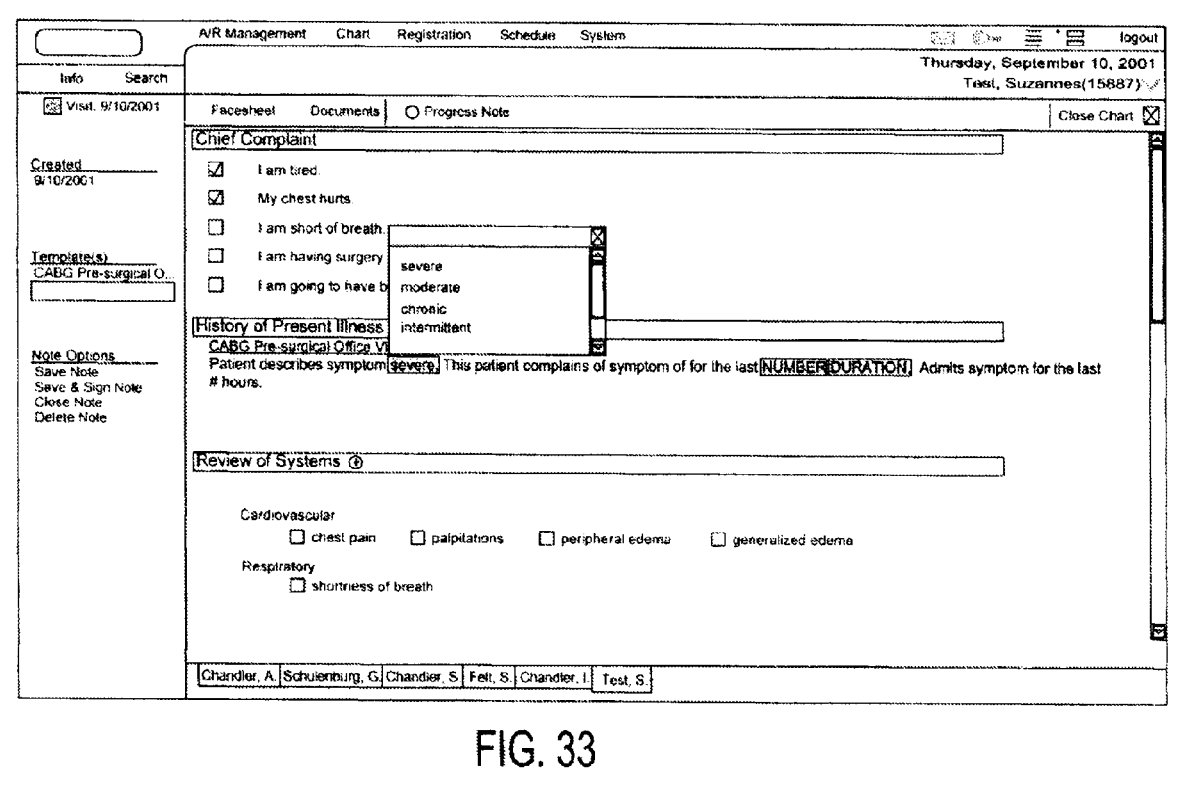

A sample Progress Note template used to generate a Progress Note document is shown in FIG. 33. The user can select to complete a progress note from the desktop, facesheet or document list. Once the user selects to create a Progress Note, a blank progress note is displayed. The user then determines if the visit displayed on the action bar is appropriate. If the user chooses to create a Progress Note without a visit link, the user can select the default visit displayed (last visit is the default) or select a new one by clicking a link button which allows the user to search for a visit date.

Once the visit date is selected, the user selects a template to use from a list of template fields that are displayed on the action bar. Several template fields can be provided to assist the user in finding the desired template, such as either a physician's template field or a nurse's template field. Upon clicking on the template field, a drop-down menu displays the user's custom templates that were earlier created, as well as any standard pre-defined system templates designed for that template field.

In FIG. 33, the user has selected to work with the template "CABG Pre-Surgical Office Visit" from the list of templates in the drop-down menu. Multiple templates may also be selected by the user by clicking another template from the list. The user can work on different templates for multiple patients, and a tab is shown at the bottom of the screen for each patient that the user is working on to enable the user to quickly switch between templates and/or patients. In addition, the name of the selected template "CABG Pre-Surgical Office Visit", is displayed above the template field and the template pre-fills into the Progress Note.

The system pre-fills all of the selected items for the Template, which were defined during the Template administration, and displays the defined template sections. Typically, the template has the following sections: Chief Complaint, History of Present Illness, Review of Systems, Physical Examination, Assessment, and Plan.

To create the completed Progress Note, the user edits the Progress Note by clicking desired findings from the patient encounter. The Chief Complaint document section builder of the template builder 48 enables the user to select the chief complaint that most closely relates to the patient's subjective description about the problem that has brought the patient to see the physician. A list of possible chief complaints, such as "I am tired" or "My chest hurts", that were associated with the template is displayed for the user to select to add to the document.

The HPI document section builder of the template builder 48 enables the user to enter information into the HPI section. Selecting the History of Present Illness header on the document will populate the field with the document view of selected descriptions associated with the template. Information can be selected in the document builder in accordance with the manner set up when the template was constructed. Information can be entered by the user in the form of a list, date stamp, input box, multiple select (select multiple choices from a predefined list of multiple choices), and demographic information. An example of a list is shown in FIG. 33, where the user's selection of "severe" has been entered into the document. Certain text may designate where the correct gender specific pronouns of he/she, himself/herself, his/her, him/her will default into the sentence.

Figure 34:
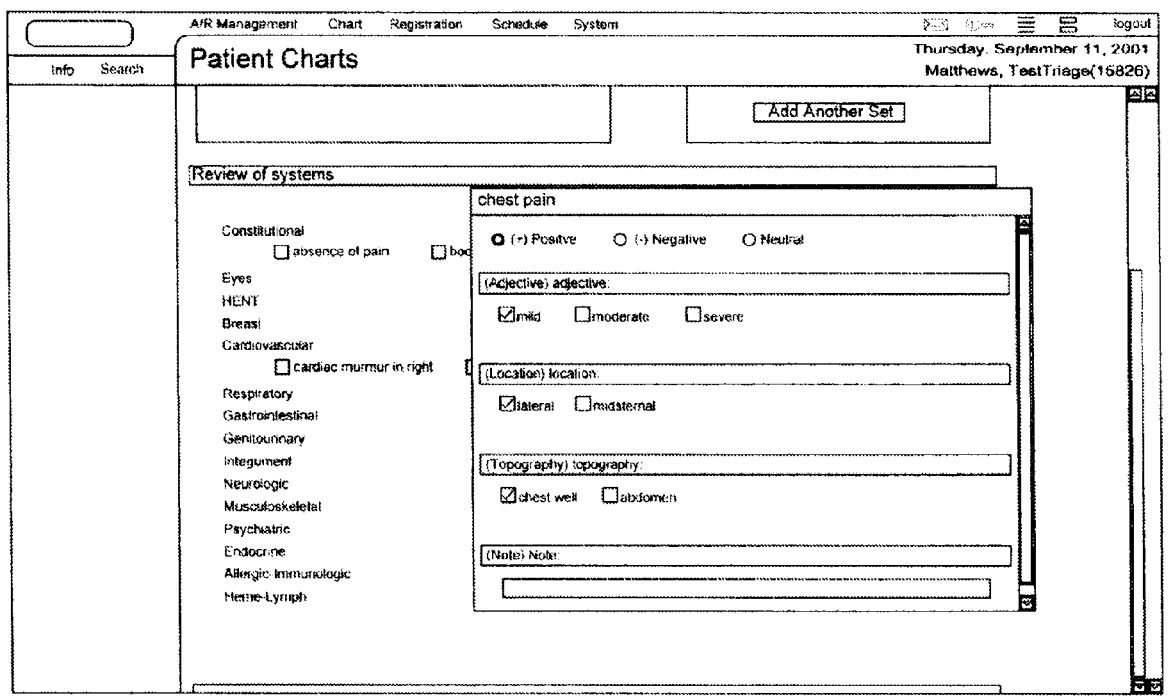

FIG. 34 shows further editing in the ROS document section being performed by the use of checkboxes. The ROS document section is an inventory of body systems obtained through a series of questions seeking to identify signs and/or symptoms which the patient may be experiencing or has experienced. The ROS document section is a vital part of the patient encounter. The ROS can be accessed from the patient chart in the triage note or from the Progress Note. When ROS is in a document, ROS will appear on the menu bar in the Template Administration page for selection by the user.

The user can complete the ROS document section based on information gathered during the patient's office visit, as the user asks the patient questions concerning particular body organs and/or regions. The review is documented in a systematic manner and certain sections can pre-fill from registration or triage to the ROS document section of the physician's Progress Note. The user may examine all systems or one or more systems, and may choose to not include the remaining systems, depending on the patient's reason for visit, physical appearance, etc. When some systems are not included in the ROS document section, those systems will not be shown in the narrative summary of the ROS. If all symptoms are neutral, the system is not included. If the system has either a negative or positive symptom, the system is included.

As each system heading of the ROS document section is selected by the user, multiple symptoms related to that system are displayed. The default settings for each symptom will be "neutral". The user may click on the checkbox next to the symptom once to change the status to "negative" (−); one click on the checkbox again changes the status to "positive" (+). In FIG. 34, the user has selected the systems, Constitutional and Cardiovascular, and the respective symptoms are displayed, such as absence of pain, cardiac murmur and chest pain. The user has selected the symptom "chest pain" as a positive status (indicating that the patient is experiencing chest pain). The negative status indicates that the patient denies a symptom, such as chest pain.

To enter more details about the positive status of a symptom, the user can click on the actual word (name of the symptom). Clicking on the word will cause the radio button to change to "positive" and a pop-up details box will appear, as shown in FIG. 34. The details box allows the user to select more detailed information, such as duration, severity, location, alleviating factors, etc. The descriptive terms have been defined by the user in the ROS administration piece. After entering a further description of the positive symptom, the descriptor appears next to the symptom name. Categories of body systems and the symptoms under each body system may be edited, added or deleted in the ROS administration piece.

As shown in FIG. 35, the Physical Exam document section builder of the template builder 48 enables the user to complete a physical exam of the patient. The user selects the PE document section associated with a pre-built template or by choosing the system and related components independent of any template and enabling the care giver to create a document describing the examination from the physician.

When the basic exam or "B" button is clicked, all systems selected for the template are pre-selected for the basic exam. When the comprehensive physical exam or "C" button is clicked, all systems selected for the template are pre-selected for the comprehensive exam. If nothing is selected under "Full Exam", then the user may select B or C for each of the systems, as shown in FIG. 35 for Cardiovascular. Only the systems selected are displayed. With each system, the user may select basic exam, comprehensive exam, or both. If nothing is selected, then the default that is displayed is both exams—the list of findings specifically included in the template being used for this document. The user may select which one of the two types of exams he wishes to document in the patient record.

The user can select findings for any of the terms in the Physical Exam document section. In the example of FIG. 35, the PE document section Cardiovascular has a subcategory to Auscultation called "Rate", "Rhythm", and "S1", which are displayed when the user selects Auscultation. By hovering over the text, a pop up box is displayed with more detailed information about selected findings. Here, the user clicks "S1" and the cascading menu for S1 displays. The user may select from this menu. In this case, whatever finding the user selects will be added to the Auscultation portion of the physical exam, and the finding is displayed.

Alternatively, the PE builder can be implemented in a manner similar to that described with respect to FIG. 23, which is for template administration. That is, a navigation sidebar can be provided that lists all the systems, and the systems and finding can be displayed with selection boxes. Values and modifiers can be associated with each finding. At any time during the document building process, the user can preview the document by selecting Preview on the navigation bar at the top of the page. All sections of the customized template are displayed on the preview page, and can be edited by the user.

Figure 36:
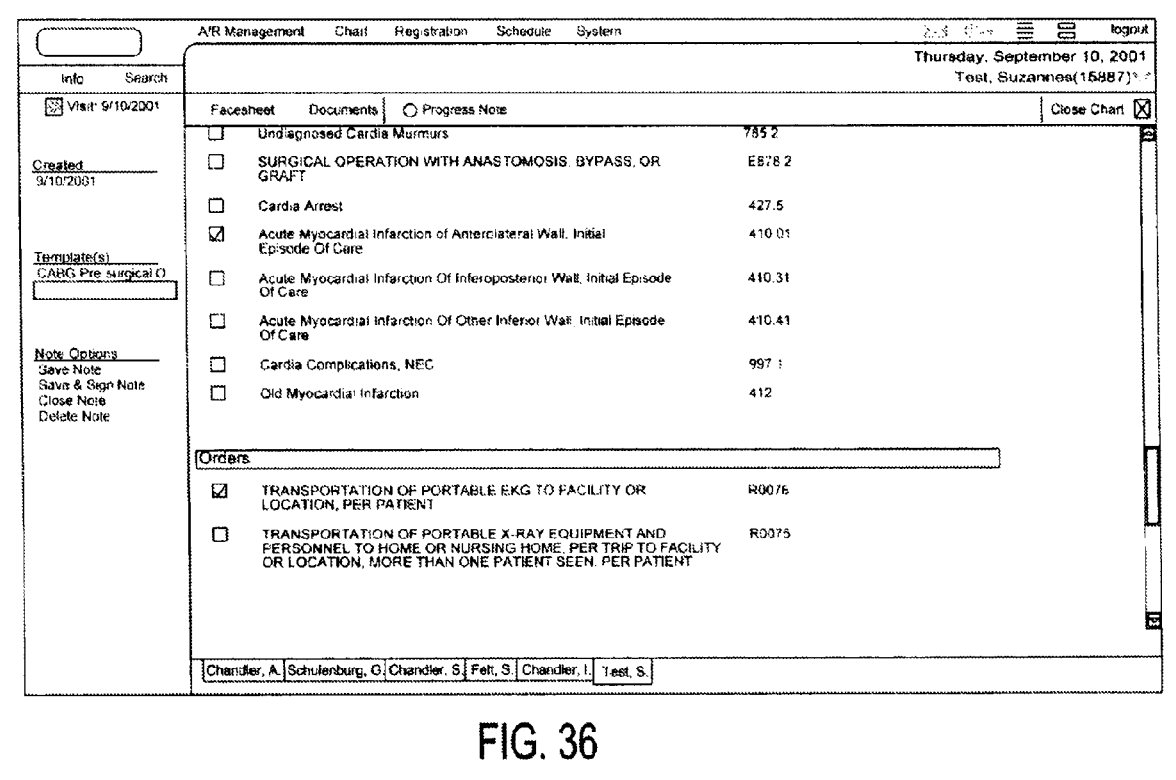

In FIG. 36, the Assessment and Plan document sections are displayed and the selections are bolded. Upon the user's selection of a diagnosis from the Assessment section, the orders, medications, and instructions of the plan section are automatically completed, as shown. The user may utilize any of the note options. The Assessment document section contains diagnoses (with related ICD-9 coding) chosen by the user in the Assessment & Plan template section builder. The Progress Note is created and the section of that document called "Assessment" displays the pre-selected diagnosis options from which the user may select the desired diagnosis or multiple diagnoses. The user selects the diagnosis or multiple diagnoses by clicking on the checkbox of the desired diagnosis.

Checkboxes can also be provided to allow a clinician to mark an item as "rule out" instead of a diagnosis. That is used when tests are ordered to rule out a certain diagnosis, so the code for that item should not be used to bill the encounter, as it is not really a diagnosis. The selected diagnosis and the associated ICD-9 code becomes bolded, as shown. Once the Progress Note is documented, it is displayed to the user in completed form.

Following a patient encounter, the clinician will usually have orders, prescriptions, and instructions for the patient. The clinician is able to document the "plan" for the patient in a section of a document which becomes part of the patient's chart, such as in the Progress Note document. These plan items can be associated with each particular diagnosis. For example, a patient who is having chest pain will typically require at least a chest x-ray, an EKG, a prescription for nitroglycerin, and a follow-up visit.

In the Order section of the document, the physician lists the orders associated with the progress note and/or office visit. The orders are linked to CPT coding. They may be the CPT codes as well as user-created orders that are linked to the CPT codes. The Orders associated with the diagnoses for this particular template are pre-filled into the Progress Note under the "Orders" section, as shown above. A checkbox to the left of each Order is present to enable the physician to choose the particular Orders for this patient. The user selects the desired Order for the patient by checking the checkbox. The selected item is bolded, and the CPT coding is placed to the right.

Figure 37:
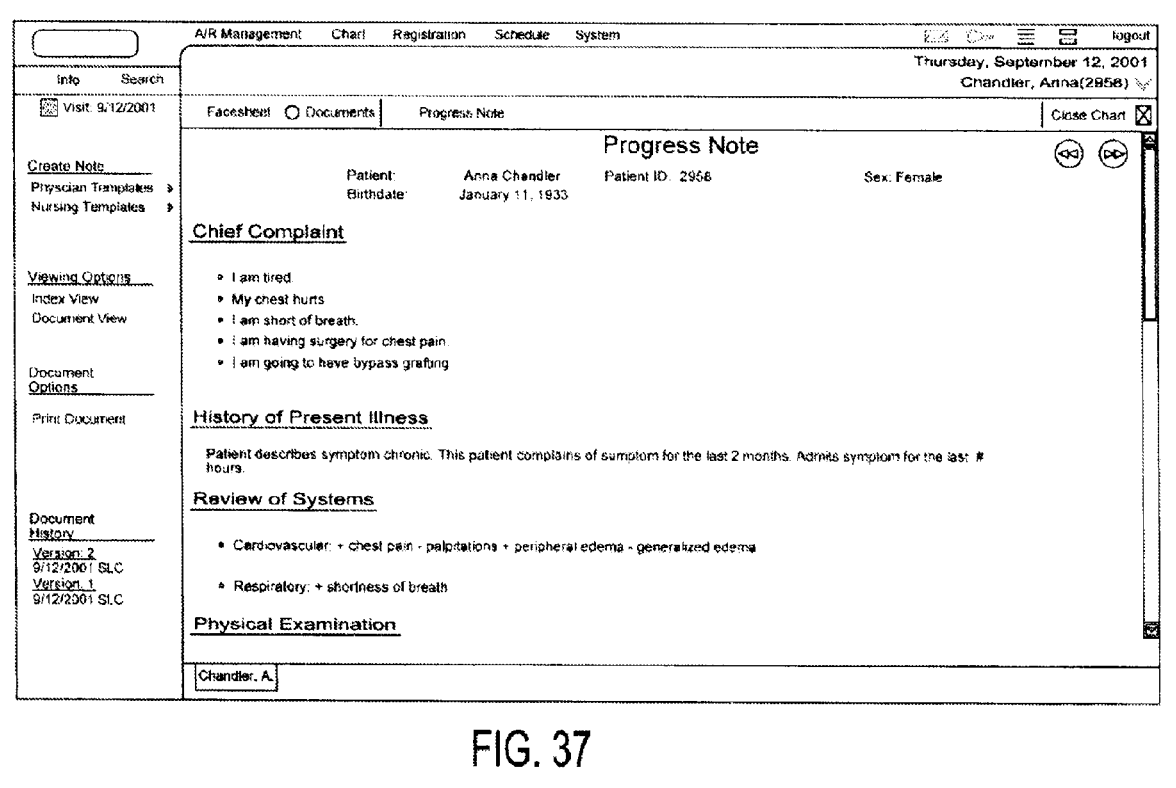
Figure 38:
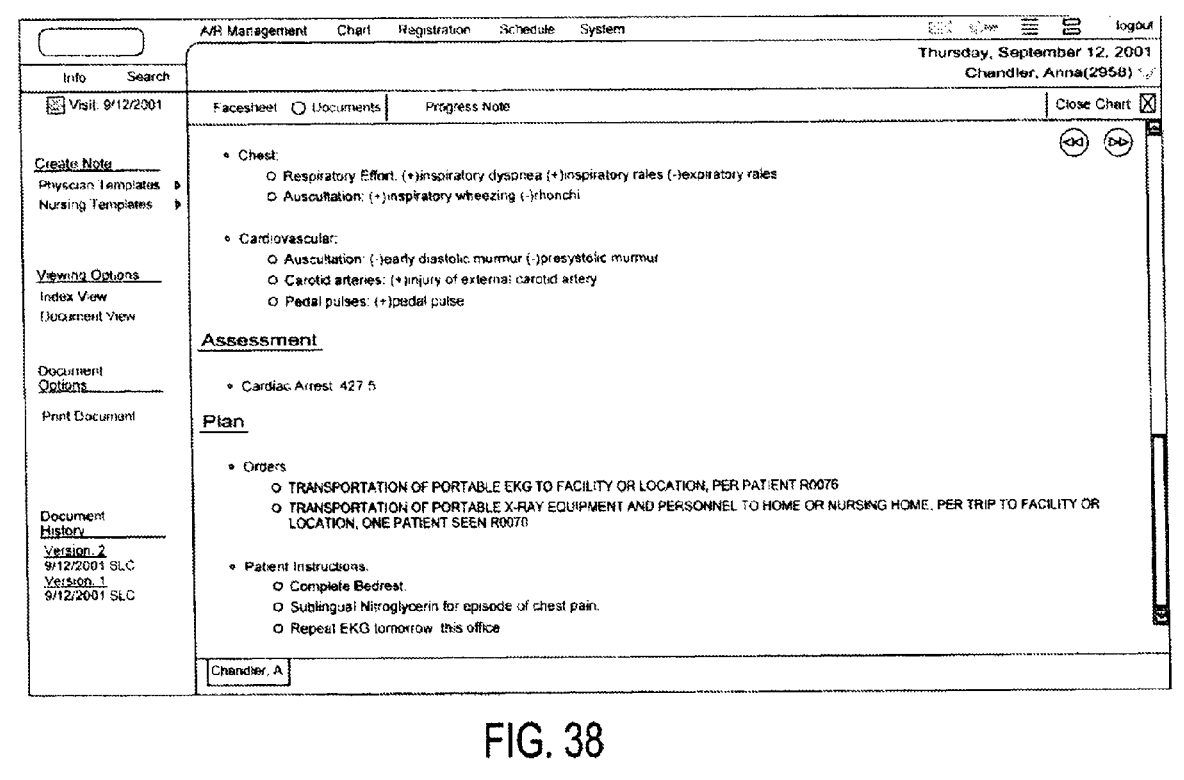
Figure 39:
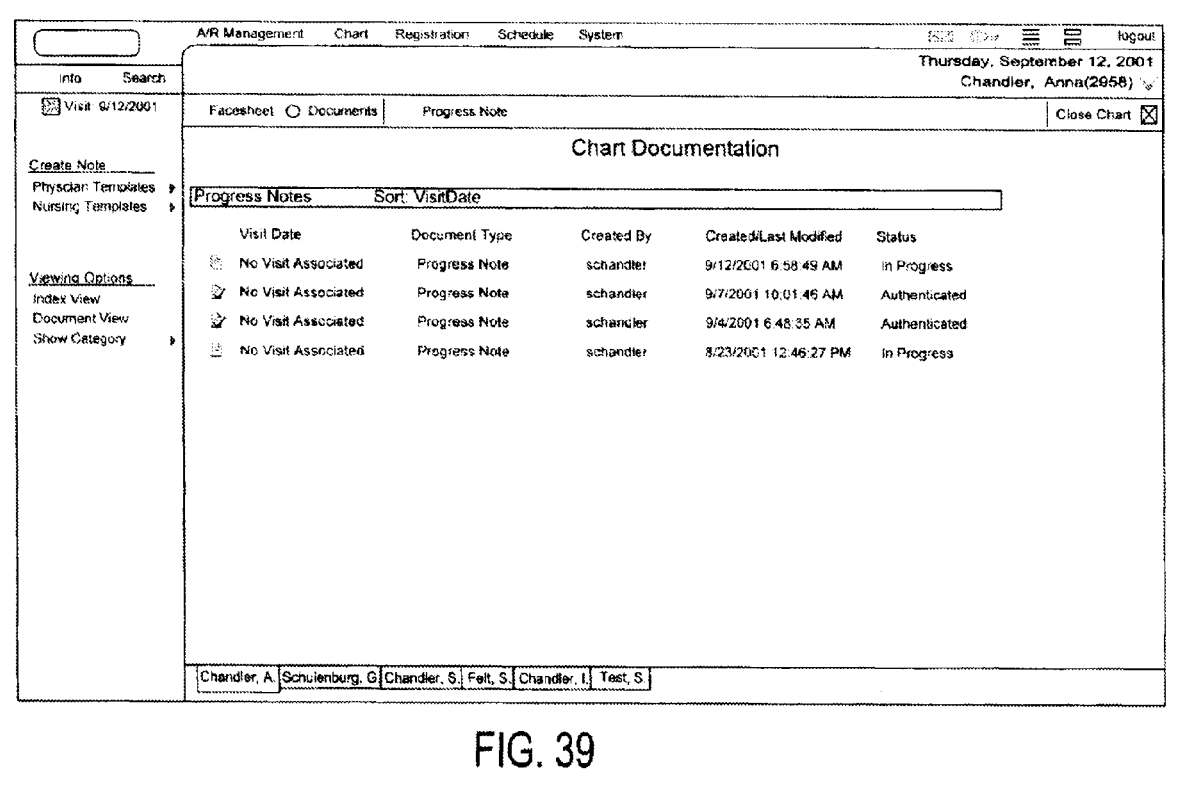

At this point, the document is complete and the user's selections are displayed as a final document, as shown in FIGS. 37 and 38. Each section is displayed, even if no entries were made to that section. However, areas that were not examined or inquired into by the clinician are not displayed, so that for instance Constitutional is not displayed under the PE section. The Progress Note, if saved or authenticated (saved & signed), is then displayed in the document list of the patient's EMR chart, FIG. 39. It may be closed, opened, or amended if saved or authenticated. If not saved, it can be deleted. The Progress Note is saved and displayed on the document list, "Chart Documentation."

Other documents can be generated by the document builder, and other medical history information can be included in a progress note as separate sections, including Past Medical History (PMH), Past Surgical History, Social History, and Family Medical History. These documents generally enable the clinician to gather information about the medical, social and family history of a patient. As an example for PMH, for instance, illnesses can be organized under the categories of the body systems they affect. The list of illnesses are pre-selected by the clinician. When specific illnesses are selected, the user may enter dates of onset and any notes concerning the situation. This function can be accessed from the other areas in the system, such as the face sheet.

Another type of document that is generated from the document builder is the H&P Note. An example of the PE section of an H&P Note is shown, for instance, in FIG. 40. Here, the system macros are listed along the left side of the page, such as Constitutional, Eyes, HENT, Neck and Chest. The user selects a system in order to display the findings and place the findings in edit mode. The user can choose option "T" to only edit the findings that were defined during the template administration, option "C" to edit all findings in the location, or option "F" to edit all findings for one or more macros. In the example, the user has selected the system Eyes, and the options All; Cond, Sclera, Lids; Pupils and Irises; and Funduscopic Exam are displayed in the order of location of the systems.

The findings are displayed adjacent the location options. In the example, the findings for the system Eyes is displayed in edit mode. When a user selects a finding name, a list of modifiers is presented for further selection by the user. For instance, the modifier can indicate the severity of the finding as being "severe", "moderate" or "mild". The user can select the appropriate modifier, which then becomes associated with the finding in the final H&P Note, whereas the findings for the system HENT are displayed with their default values and modifiers which have been selected for this system in the PE template builder upon which this note is based.

A drawing can also be incorporated into the H&P note or progress note. The drawing allows the user to select anatomical images from a library, draw on them and embed them into documents and notes to better document medical information that might be difficult to communicate with words alone. For instance, the physician can select an image of a patient's abdomen and draw the location of previous surgical scars, changes in discoloration or area of infection between visits. As the H&P or progress note is being created, the user has the option of selecting to include a drawing. The user then selects the desired image from the library of images. Preferably, this is achieved by displaying an image of a full human body, and allowing the user to focus in on a specific area. Once the desired image is displayed, the user then draws the desired shape and color to add to that image.

Order Management

An additional system feature includes clinical alerts, reminders and tracking. These features allow clinicians to more effectively serve their patients. Once a patient leaves the office, the system tracks the status of requested consultations and tests, and provides respective alerts and reminders to the respective users. The alerts can be requested by the clinician or based on standard health maintenance protocols. It automates the process of reviewing and tracking incoming and pending order results so that fulfillment is documented and failure to fulfill is investigated and remedied.

Clinicians can also define alerts, reminders and recommendations for treatment based on the user's preferred treatment algorithms or on insurance rules for reimbursement. Users can also define links to internal and external resources for clinician reference and patient education.

The system also has automated prescription writing, and interaction reference access. Electronic transmission capability to fulfillment resource and refill management is automated, thereby reducing prescription and refill processing. The system automates fulfillment of orders by real-time transfer of instructions directly from an encounter documentation template to the fulfillment source, without the need to duplicate the instructions in an intervening document or data entry process.

For example, prescriptions are automatically electronically transmitted directly from the encounter documentation to the participating pharmacy, lab orders are automatically transmitted directly to the participating lab with supporting diagnoses and prior approval included, diagnoses and coding are automatically transferred from the encounter documentation to the billing module, and follow-up appointment requests are directly transferred from the encounter documentation to the scheduling module (i.e., part of the practice management module).

Prescription refills are also automated, so that the clinician need only make a single selection for refills requiring no changes. The clinician need not write a new prescription for the refill, the refill is automatically documented in the patient's chart, and the instructions are electronically transmitted to the pharmacy.

Another feature of the system is order placement which integrates with billing processes to reduce charge entry efforts and ensure that third-party reimbursement requirements are met.

Messaging

The system supports communication between the clinician and other staff members from any point in the facility at any time. Messaging is implemented by a messaging component 22 of the framework module 20, that creates, stores and retrieves intra-office communication. Messages can also be generated by the system to indicate situations where action is required. Messages are automatically added to the patient chart, when the user chooses to "attach" a patient to the message.

The messaging module gives near real time updates that new messages have arrived. The customer workstation 12 is in contact with the main services server 10 every few seconds to check if new messages have arrived. A service is used, as opposed to a web page, to keep the constant pinging from affecting the application. The messaging module maintains an icon to the desktop that indicates that a new message has arrived. The system indicates to the user that a new message has arrived, which the user can then retrieve.

When composing a message, once a Patient is selected, the corresponding Patient Frame overlays in the body of the Message. If there is a photograph of the patient displayed in the Patient Frame, the photo will also be displayed in the Message. If there is a Patient Name in the Patient field, the Message will be associated with that Patient. All Messages composed and sent by the user are audit logged, indicating that the action was a sent message, the patient ID, the sender and the recipient, and the time.

The messaging system is provided with predefined response templates for common requests and routine calls and questions. Responses generate a note in the patient's chart.

Patient Access

The system provides secured and structured two-way communication between the patient and the clinician. The patient can submit post-treatment outcome results and status to the clinician in a predefined template. That allows the clinician to analyze the effectiveness of the treatment provided without the burden of reading free-text email. The increased patient interaction strengthens the clinician-patient relationship and increases the efficiency in scheduling appointments, registration, the interview process and requesting prescription refills. That is not only more convenient for the patient, but allows the clinician practice to shift a great deal of data entry from their clerical staff to the patient.

Patients access the system through a centralized web portal, such as their clinician's website. The web portal allows the patient to perform limited functions with respect to appointment scheduling, patient interviews, prescription refill requests, personal health record access, appointment follow-up information and electronic consults. Patients can choose to be reminded of appointments electronically at various intervals before visits. Data from paper records can also be moved to the personal health record (PHR). A PHR allows a patient to track visits to a clinician, medications, in-home observations of blood sugar, vital signs, etc.

Audit Logging and Security

Audit logging is performed throughout the system to assist system administrators in enforcing practice policies and compliance with regulations. Security options include username and password and/or biometric identification for access control. The username allows role-based and/or user-based control of permission to use various system functions.

Overview of Features

The system is designed to be intuitive to the user and provide a secure environment that can be accessed at the clinician's office or at a remote site. The system also interfaces to email and the clinician's website, and provides support for phone messaging, patient education materials, website, direct patient data entry via the web, email, and ROI studies.

The system eliminates the need for paper charts, thereby reducing the amount of office space allocated to storing patient records, and allowing electronic transfer of information between practices. All incoming paper documents and existing paper patient files, can be scanned or otherwise entered into the system and the paper files eliminated. The patient's EMR can be accessed at any time and from any location, thereby eliminating manual chart pulls and misplaced paper files. The number of chart pulls is reduced by about 50% within six months of implementing the present invention, and about 85% at twelve months.

Once the system is fully implemented, transcription costs could be eliminated, malpractice premiums could be reduced by about 3-5% from insurance companies that offer physicians who use an EMR a discount due to the increased detail of documentation with an EMR as opposed to dictation or handwriting, and staff savings of about 15%. Perhaps most importantly, clinician productivity gain increases by about 20% after only twelve months, resulting in a savings of about $7,000-15,000 per clinician each year.

The information provides rapid and concise malpractice proof to help the user defend against malpractice claims and HCFA audits. The system also offers the clinician prescription assistance with brand name and generic pricing and dosage, national drug codes, medication lists, allergy cross-checks (drug-drug, drug-food, drug-disease interactions), and side affects. The entry of charges is automated and the resulting documentation is checked for compliance with billing and claims filings.

Although the preferred embodiment of the invention is for use at a clinician's practice, the system can be implemented at the office of any service professional. The system is configurable at the user and practice levels, so that a practice can assign specific duties and responsibilities to employees to maximize overall office productivity without restrictions imposed by existing practice management and EMR systems.

The foregoing description and drawings should be considered as illustrative only of the principles of the invention. The invention is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

We claim:

1. A template builder building a custom template that will be used by a health care provider to generate an electronic document for a patient during a subsequent encounter with the patient, the template builder comprising:

means for a user to select a type of electronic document that will be generated from the custom template during the subsequent encounter with the patient, the type of electronic document selected defining one or more predefined sections that will be built in the custom template; and means for building one or more predefined sections in the custom template that is configured for the user to draft and/or select one or more sentences in at least one of the one or more predefined sections and that is configured for the user to define and/or select one or more fields for completing at least one of the one or more sentences, wherein one or more fields include at least one of a default control type that is subsequently and automatically populated with the patient information during the encounter with the patient, an input box that creates a point in a sentence where data can subsequently be manually input by the user during the encounter with the patient, and a select list that creates a list of different options that can subsequently be chosen by the user as text for completing at least one of the one or more sentences during the encounter with the patient.

2. The template builder of claim 1, wherein the one or more predefined sections are based on a clinical document architecture (CDA) defined by Health Level 7(HL7).

3. The template builder of claim 1, wherein
   the user can select at least one of the one or more sentences by topic from one or more predefined sentences; and
   elements of the one or more predefined sentences that are required to submit a patient bill for payment are denoted by a different color.

4. The template builder of claim 1, wherein
   the electronic document built for the patient is built with an electronic date/time stamp that corresponds to the date and time of the encounter with the patient.

5. The template builder of claim 1, further comprising
   means for the user to define and/or select one or more body systems and one or more symptoms related to each body system in at least one of the one or more predefined sections,
   wherein the user can subsequently choose from the defined and/or selected one or more body systems and one or more symptoms during the encounter with the patient to identify specific symptoms to which the patient admits.

6. The template builder of claim 5, wherein
   each of the one or more symptoms defined will be available for selection in subsequent template building operations performed with the template builder.

7. The template builder of claim 5, further comprising
   means for the user to configure one or more worksheets or checklists in at least one of the one or more predefined sections for performing a physical examination of the one or more body systems during the encounter with the patient, the one or more worksheets or checklists being configured to include one or more findings associated with each of the body systems being examined and being available to subsequently be chosen by the user during the encounter with the patient.

8. The template builder of claim 7, further comprising
   means for the user to select and/or locate and select one or more diagnoses in at least one of the one or more predefined sections, the selected and/or located and selected one or more diagnoses being associated with the one or more findings and being available to subsequently be chosen by the user during the encounter with the patient.

9. The template builder of claim 8, further comprising
   means for a user to define and/or select one or more plans for treating the patient in at least one of the one or more predefined sections, the defined and/or selected one or more plans for treating the patient corresponding to the one or more diagnoses and being available to subsequently be chosen by the user during the encounter with the patient.

10. The template builder of claim 9, further comprising
    means for a user to define and/or select one or more chief complaints in at least one of the one or more predefined sections,
    wherein the user can subsequently choose from the defined and/or selected one or more chief complaints during the encounter with the patient, and
    wherein the one or more sentences drafted and/or selected, the one or more body systems and one or more symptoms defined and/or selected, the one or more worksheets or checklists configured, the one or more diagnoses selected and/or located and selected, and the one or more plans for treating the patient defined and/or selected each relate to the one or more chief complaints defined and/or selected.

11. The template builder of claim 9, wherein
    at least one of the one or more findings, the one or more diagnoses, and the one or more plans for treating the patient is automatically associated with one or more of Evaluation and Management (E/M) coding, International Code of Diseases (ICD) coding, Current Procedural Terminology (CPT) coding, and HCFA Common Procedure Coding System (HCPCS) coding.

12. The template builder of claim 11, further comprising
    means for automatically generating an electronic superbill for billing the patient at checkout and for electronically filtering and sorting insurance claims using the one or more of ICD coding, CPT coding, and HCPCS coding.

13. A method for building a custom template that will be used by a health care provider to generate an electronic document for a patient, the method being embodied on a computer readable medium and executed by a processor to perform steps comprising:

having a user to select a type of electronic document that will be generated from the custom template during the subsequent encounter with the patient, the type of electronic document selected defining one or more predefined sections that will be built in the custom template; and having the user building one or more predefined sections in the custom template by having the user draft and/or select one or more sentences in at least one of the one or more predefined sections and by having the user to define and/or select one or more fields for completing at least one of the one or more sentences, wherein one or more fields include at least one of a default control type that is subsequently and automatically populated with the patient information during the encounter with the patient, an input box that creates a point in a sentence where data can subsequently be manually input by the user during the encounter with the patient, and a select list that creates a list of different options that can subsequently be chosen by the user as text for completing at least one of the one or more sentences during the encounter with the patient.

14. The method of claim 13, wherein the user can select at least one of the one or more sentences by topic from one or more predefined sentences; and elements of the one or more predefined sentences that are required to submit a patient bill for payment are denoted by a different color.

15. The method of claim 13, wherein the electronic document built for the patient is built with an electronic date/time stamp that corresponds to the date and time of the encounter with the patient.

16. The method of claim 13, further comprising the step of having the user define and/or select one or more body systems and one or more symptoms related to each body system in at least one of the one or more predefined sections, wherein the user can subsequently choose from the defined and/or selected one or more body systems and one or more symptoms during the encounter with the patient to identify specific symptoms to which the patient admits.

17. The method of claim 16, wherein each of the one or more symptoms defined will be available for selection in subsequent template building operations performed with the template builder.

18. The method of claim 16, further comprising the step of having the user configure one or more worksheets or checklists in at least one of the one or more predefined sections for performing a physical examination of the one or more body systems during the encounter with the patient, the one or more worksheets or checklists being configured to include one or more findings associated with each of the body systems being examined and being available to subsequently be chosen by the user during the encounter with the patient.

19. The method of claim 18, further comprising the step of having the user select and/or locate and select one or more diagnoses in at least one of the one or more predefined sections, the selected and/or located and selected one or more diagnoses being associated with the one or more findings and being available to subsequently be chosen by the user during the encounter with the patient.

20. The method of claim 19, further comprising the step of having the user define and/or select one or more plans for treating the patient in at least one of the one or more predefined sections, the defined and/or selected one or more plans for treating the patient corresponding to the one or more diagnoses and being available to subsequently be chosen by the user during the encounter with the patient.

21. The method of claim 20, further comprising the step of having the user define and/or select one or more chief complaints in at least one of the one or more predefined sections, wherein the user can subsequently choose from the defined and/or selected one or more chief complaints during the encounter with the patient, and wherein the one or more sentences drafted and/or selected, the one or more body systems and one or more symptoms defined and/or selected, the one or more worksheets or checklists configured, the one or more diagnoses selected and/or located and selected, and the one or more plans for treating the patient defined and/or selected each relate to the one or more chief complaints defined and/or selected.

22. The method of claim 19, wherein at least one of the one or more findings, the one or more diagnoses, and the one or more plans for treating the patient is automatically associated with one or more of Evaluation and Management (E/M) coding, International Code of Diseases (ICD) coding, Current Procedural Terminology (CPT) coding, and HCFA Common Procedure Coding System (HCPCS) coding.

23. The method of claim 22, further comprising the step of automatically generating an electronic superbill for billing the patient at checkout and for electronically filtering and sorting insurance claims using the one or more of ICD coding, CPT coding, and HCPCS coding.

24. A template builder building a custom template that will be used by a health care provider to generate an electronic document for a patient during a subsequent encounter with the patient, the template builder comprising:

a chief complaint component for a user to define one or more chief complaints in a chief complaint section of the custom template;

a history of illness component for the user to draft and/or select one or more sentences and for the user define and/or select one or more fields for completing at least one of the one or more sentences in a history of illness section of the custom template, the one or more fields including at least one of a default control type that is subsequently and automatically populated with patient information during the subsequent encounter with the patient, an input box that creates a point in a sentence where data can be manually input by the user during the subsequent encounter with the patient, and a select list that creates a list of different options that can be chosen by the physician as text for completing at least one of the one or more sentences during the subsequent encounter with the patient;

a review of systems component for the user to define and/or select one or more body systems associated with the chief complaint and one or more symptoms related to each body system in a review of systems section of the custom template, the one or more body systems and one or more symptoms being available to be chosen by the user during the encounter with the patient to identify specific symptoms to which the patient admits;

a physical examination component for the user to configure one or more worksheets or checklists for performing a physical examination of the one or more body systems associated with the chief complaint in a physical examination section of the custom template, the one or more worksheets or checklists being configured to include one or more findings associated with each of the body systems being examined from which the user can subsequently choose during the encounter with the patient;

an assessment component for the user to locate and select one or more diagnoses associated with the one or more findings in an assessment section of the custom template the user being able to choose from one or more diagnoses during the subsequent encounter with the patient; and a plan component for a user to define one or more plans for treating the patient corresponding to the one or more diagnoses in an plan section of the custom template the user being able to choose from one or more plans during the subsequent encounter with the patient wherein the chief complaint section, the history of illness section, the review of systems section, the physical examination section, the assessment section, and the plan section are compiled by the template builder to generate the electronic progress note that will be used by the user during the subsequent encounter with the patient.

* * * * *